(12) United States Patent
Han

(10) Patent No.: US 9,265,810 B2
(45) Date of Patent: *Feb. 23, 2016

(54) PHARMACEUTICAL COMPOSITION AND METHODS FOR MODULATING IMMUNE SYSTEM, PREVENTING, PRETREATING AND/OR TREATING CANCERS

(71) Applicant: Hong Kong Baptist University, Hong Kong (HK)

(72) Inventor: Quanbin Han, Hong Kong (HK)

(73) Assignee: HONG KONG BAPTIST UNIVERSITY, Kowloon Tong, Kowloon (HK)

(*) Notice: Subject to any disclaimer, the term of this patent is extended or adjusted under 35 U.S.C. 154(b) by 0 days.

This patent is subject to a terminal disclaimer.

(21) Appl. No.: 14/656,712

(22) Filed: Mar. 13, 2015

(65) Prior Publication Data

US 2015/0196611 A1    Jul. 16, 2015

Related U.S. Application Data

(63) Continuation-in-part of application No. 14/033,528, filed on Sep. 23, 2013, now Pat. No. 9,005,676.

(51) Int. Cl.
| | | |
|---|---|---|
| *A01N 65/00* | (2009.01) |
| *A61K 36/481* | (2006.01) |
| *A61K 36/344* | (2006.01) |
| *A61K 36/074* | (2006.01) |
| *A61K 31/337* | (2006.01) |
| *A61K 47/48* | (2006.01) |
| *A61K 31/7068* | (2006.01) |

(52) U.S. Cl.
CPC ............. *A61K 36/481* (2013.01); *A61K 31/337* (2013.01); *A61K 31/7068* (2013.01); *A61K 36/074* (2013.01); *A61K 36/344* (2013.01); *A61K 47/48284* (2013.01)

(58) Field of Classification Search
CPC ..................................................... A61K 36/00
USPC ........................................................ 424/725
See application file for complete search history.

(56) References Cited

U.S. PATENT DOCUMENTS

2006/0110473 A1* 5/2006 Xie ...................... A61K 36/344
                                                                    424/757

* cited by examiner

*Primary Examiner* — Michael Meller
(74) *Attorney, Agent, or Firm* — Ella Cheong Hong Kong; Sam T. Yip

(57) ABSTRACT

This invention provides a pharmaceutical composition for modulating immune system comprising at least one polysaccharide extracted from *Radix Astragali, Radix Codonopsis, Ganoderma sinense*, or mixtures thereof, and their extraction process. The present invention further relates to a method of modulating immune system by applying said pharmaceutical composition to a subject suffering from cancers, and a method of preventing and/or pretreating and/or treating cancers in the subject, where said method comprises applying said pharmaceutical composition before/during chemotherapy.

16 Claims, 24 Drawing Sheets

A

B

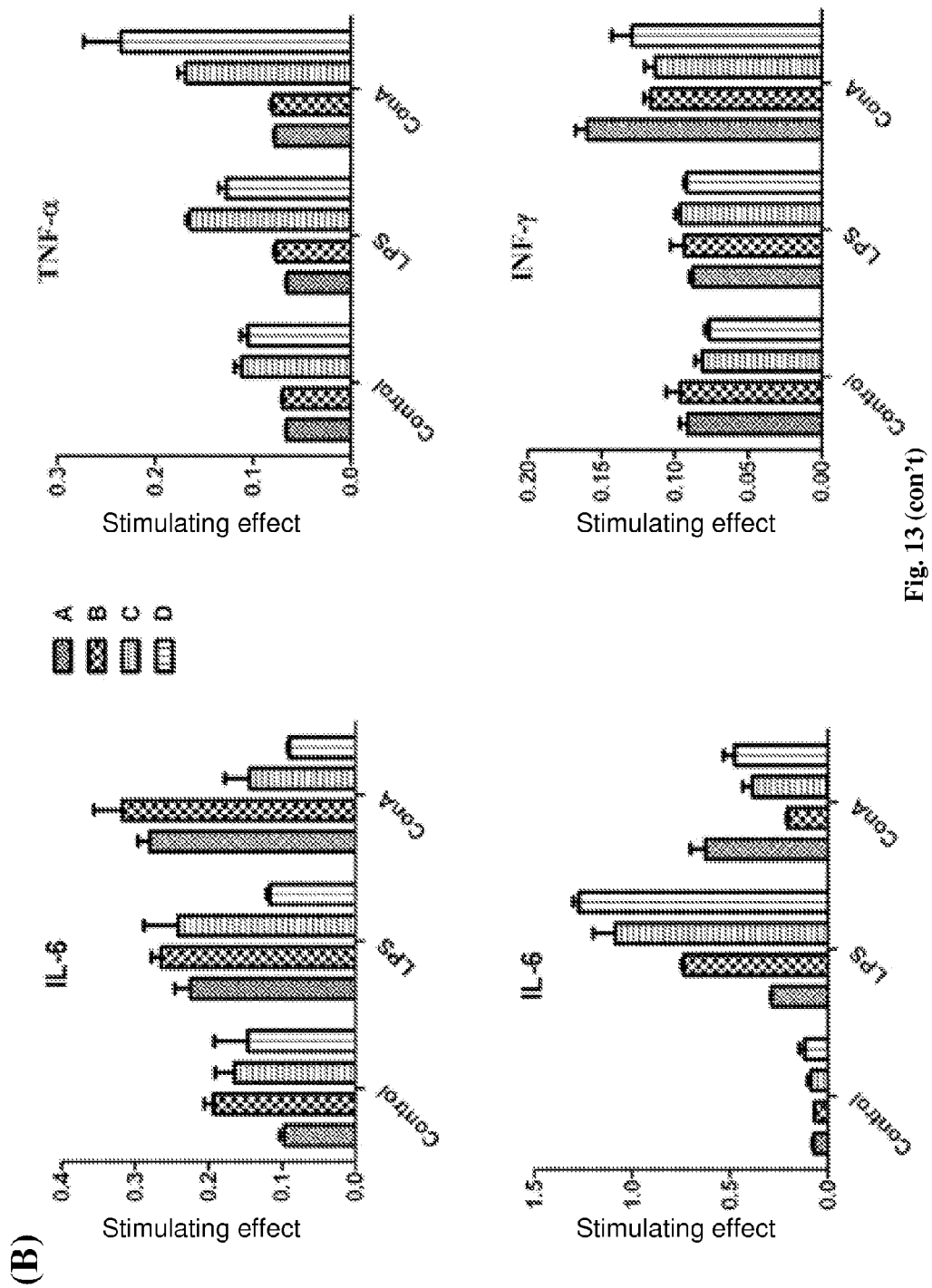
Fig. 13 (con't)

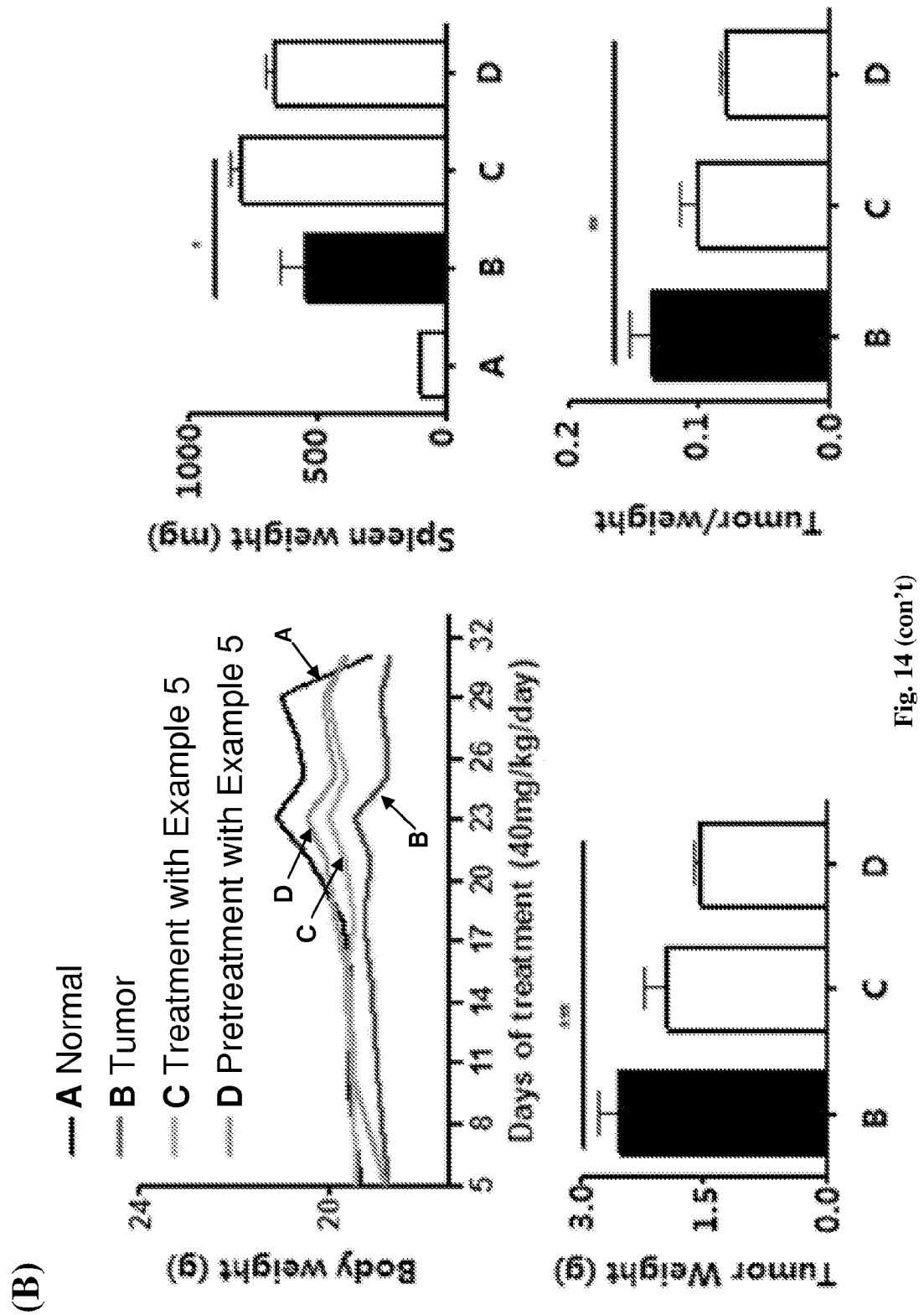
Fig. 14 (con't)

PHARMACEUTICAL COMPOSITION AND METHODS FOR MODULATING IMMUNE SYSTEM, PREVENTING, PRETREATING AND/OR TREATING CANCERS

CROSS-REFERENCE TO RELATED APPLICATIONS

This application is a continuation-in-part application of U.S. Non-Provisional patent application Ser. No. 14/033,528 filed Sep. 23, 2013, which claims the benefit of U.S. Provisional Patent Application Ser. No. 61/703,878 filed Sep. 21, 2012 and is hereby incorporated by reference in its entirety. The literatures HAN, X.-Q.; CHAN, B. C. L.; YU, H.; YANG, Y.-H.; HU, S.-Q.; KO, C.-H.; DONG, C.-X.; WONG, C.-K.; SHAW, P.-C.; FUNG, K.-P.; LEUNG, P.-C.; HSIAO, W.-L.; TU, P.-F.; HAN, Q.-B. Structural characterization and immuno-modulating activities of a polysaccharide from *Ganoderma sinense*. Int. J. Biol. Macromol. November 2012, Vol. 51, No. 4, pages 597-603; HAN, X.-Q.; CHAN, B. C. L.; DONG, C.-X.; YANG, Y.-H.; KO, C.-H.; YUE, G. G.-L.; CHEN, D.; WONG, C.-K.; LAU, C. B.-S.; TU, P.-F.; SHAW, P.-C.; FUNG, K.-P.; LEUNG, P.-C.; HSIAO, W.-L.; HAN, Q.-B. Isolation, Structure Characterization, and Immuno-modulating Activity of a Hyperbranched Polysaccharide from the Fruiting Bodies of *Ganoderma sinense*. J. Agric. Food Chem. April 2012, Vol. 60, No. 17, pages 4276-4281; and YIN, J.-Y.; CHAN, B. C.-L.; YU, H.; LAU, I. Y.-K.; HAN, X.-Q.; CHENG, S.-W.; WONG, C.-K.; LAU, C. B.-S. XIE, M.-Y.; FUNG, K.-P.; LEUNG, P.-C.; HAN, Q.-B. Separation, structure characterization, conformation and immunomodulating effect of a hyperbranched heteroglycan from *Radix Astragali*. Carbohydrate Polymers. 4 Jan. 2012, Vol. 87, No. 1, pages 667-675; CHOU T C, TALALAY P. Quantitative analysis of dose-effect relationships: the combined effects of multiple drugs or enzyme inhibitors. Adv Enzyme Regul, 1984, 22, 27-55; Z. J. JIN, Addition in drug combination. Acta Pharmacol Sin, 1980, 1, 70-76 are also hereby incorporated by reference in their entirety.

FIELD OF INVENTION

This invention provides a pharmaceutical composition for modulating immune system comprising at least one polysaccharide extracted from *Radix Astragali, Radix Codonopsis, Ganoderma sinense*, or mixtures thereof, and their extraction process. It further relates a method of modulating immune system by applying said pharmaceutical composition, and a method of preventing and/or pretreating and/or treating cancers which comprises applying said pharmaceutical composition before/during chemotherapy.

BACKGROUND OF INVENTION

Although great advance in the treatment of commonly seen cancers has been achieved by combined use of chemotherapy, surgery, and radiotherapy, cancer therapy still faces many challenges in early diagnosis, metastasis, drug resistance, and notorious toxicity of therapeutic agents to normal cells.

Combining anticancer agents with different mechanisms is a common strategy to improve overall efficacy; the combined use of immunotherapy and chemotherapy is one example. Nevertheless, all the agents used themselves are toxic and incur drug resistance; gemcitabine is a good example.

The medicinal herbs called Qi-tonics in Chinese medicines, like ginseng, are also used in the fight against cancers as a popular option of alternative and complementary therapy. These herbal medicines are traditionally used in the form of decoction and are usually rich in polysaccharides. Many of these polysaccharides have been shown to enhance immune system and to suppress tumor growth in various animal models.

Chinese Medicine has a golden therapy strategy: the combined use of tonifying medicines and those having dispelling function. This strategy may fit cancer therapy right: not only to kill the cancer cells, but also to strengthen the body's vital energy (healthy Qi) and restore proper and healthy cell growth. A good example is Shen Qi Fu Zheng Injection (SQFZ Injection) from Livzon Group, which synergy with chemotherapy in cancer clinic has been proved in China and therefore brought a big gross profit of HK$0.5 billion in the past half year. However, this product is facing severe technical challenge like other Chinese herbal injections, because the Chinese Government has increased the requirements of safety and quality control for this special kind of medicinal preparation.

As illustrated in FIG. 1, SQFZ Injection is derived from the water extract of *Radix Astragali* and *Radix Codonopsis* after removal of precipitate in 80% ethanol. On the other hand, the removed precipitate, also called production waste, is the typical crude polysaccharide fraction, which shares the same production protocol.

Modern scientific studies have demonstrated that *Astragalus* polysaccharides exhibit immuno-enhancing effects in vitro and in vivo. Chinese patent application CN1985877A discloses a composition containing *Radix Astragali* which strengthens immunity, prevents or treats respiratory tract infection, allergic rhinitis, damage of liver caused by glycogen reduction or antitumor medicine, viral hepatitis, regulates blood viscosity and reduces blood fat.

Combined use of *Radix Astragali* with other herbs has been reported. China patent CN1059800C discloses an injectable composition containing ginseng and *Radix Astragali* for treatment of immunodeficiency and immune disorder-related diseases. Chinese patent CN1290512C discloses a composition containing ginseng polysaccharide and *Astragalus* polysaccharide as an injectable formulation for treatment of neoplastic diseases. US patent application 2006/0110473 discloses a composition containing *Radix Codonopsis* and *Radix Astragali* for preparation of an immuno-regulator and medicaments for the treatment of ischemic heart diseases and acute lung injury. Chinese patent CN1895337B discloses a composition containing *Radix Codonopsis* and *Radix Astragali* for prolonging mortality and improving quality of life in patients of latter-phase cancer, and its preparation into injections, capsules and tablets.

However, knowledge about the chemistry of *Astragalus* polysaccharides is still limited. It is hard to identify if the same sample was studied in different laboratories and it is also hard to compare their bioactivities.

Therefore, the present invention provides a pharmaceutical composition for modulating immune system comprising at least one polysaccharide extracted from *Radix Astragali, Radix Codonopsis, Ganoderma sinense*, or mixtures thereof. While common extraction methods stated in the abovementioned prior art discard the ethanol precipitate as production waste, the present invention provides a process for extracting the polysaccharides from the production waste. Also provided is a method of modulating immune system by applying said pharmaceutical composition and a method of preventing and/or pretreating and/or treating cancer which comprises applying said pharmaceutical composition before/during chemotherapy.

Citation or identification of any reference in this section or any other section of this application shall not be construed as an admission that such reference is available as prior art for the present application.

SUMMARY OF INVENTION

According to a first aspect of the present invention, there is provided a pharmaceutical composition for modulating immune system, comprising at least one polysaccharide extracted from *Radix Astragali, Radix Codonopsis, Ganoderma sinense*, or mixtures thereof.

In a first embodiment of the first aspect, the polysaccharide has a molecular weight in the range of 500-2,500 kDa, 600-2,000 kDa, or 700-1,900 kDa.

In a second embodiment of the first aspect, the polysaccharide comprises one or more constituents selected from the group of glucose, galactose, mannose, rhamnose, arabinose, their dextrorotary and levorotary compounds, and combinations thereof.

In a third embodiment of the first aspect, any two constituents of the polysaccharide is in the molar ratio ranging from 1:30 to 30:1, 1:20 to 20:1, or 1:10 to 10:1.

In a fourth embodiment of the first aspect, the polysaccharide comprises glucose, galactose and mannose as constituents in the molar ratio of 4.7:27.1:1.0.

In a fifth embodiment of the first aspect, the polysaccharide comprises rhamnose, arabinose, glucose, galactose and galacturonic acid as constituents in the molar ratio of 0.03:1.00:0.27:0.36:0.30.

In a sixth embodiment of the first aspect, the polysaccharide comprises mainly glucose and trace amounts of galactose and mannose as constituents.

In a seventh embodiment of the first aspect, the polysaccharide has a hyperbranched structure.

In an eighth embodiment of the first aspect, the polysaccharide comprises at least one sugar residue selecting from the group consisting of 1,2,4-linked Rhap, α-1,4-linked Glcp, α-1,4-linked GalAp6Me, β-1,3,6-linked Galp, α-T-Araf, α-1,5-linked Araf, T-linked Araf, T-linked Glcp, T-linked Galp, (1→6)-linked-β-D-glucopyranosyl, (1→4)-linked-β-D-glucopyranosyl, (1→3)-linked-β-D-glucopyranosyl, non-reducing end β-D-glucopyranosyl, t-, 1,3-, 1,4-, 1,6-, 1,3,4- and 1,3,6-linked Glcp, t-linked Galp, 1,6-linked Manp, and combinations thereof.

In a ninth embodiment of the first aspect, the polysaccharide comprises a backbone of 1,6-linked-β-D-glucopyranosyl residues and branches at the O-3 position of every two sugar residues along the backbone.

In a tenth embodiment of the first aspect, the polysaccharide further comprises side chains containing 1,3-, 1,4-linked-β-D-glucopyranosyl, and non-reducing end β-D-glucopyranosyl residues.

In an eleventh embodiment of the first aspect, the polysaccharide has a protein content of 1-20% or 5-15%.

According to a second aspect of the present invention, there is provided a process of extracting polysaccharides from *Radix Astragali, Radix Codonopsis, Ganoderma sinense*, which comprises:
a) Carrying out one or more solid/liquid extractions on *Radix Astragali, Radix Codonopsis* or *Ganoderma sinense* to obtain a liquid extract;
b) Adding an organic solvent into the liquid extract to induce precipitation;
c) Centrifuging and filtering the mixture in (b) to obtain a precipitate;
d) Drying the precipitate to yield crude polysaccharides; and
e) Purifying the crude polysaccharides by ion-exchange chromatography and/or gel-permeation chromatography,
wherein the eluents from (e) include water, bases such as sodium hydroxide, and salt solutions such as sodium chloride solution.

According to a third aspect of the present invention, there is a method of preventing and/or pretreating and/or treating cancers, which comprises applying the abovementioned pharmaceutical composition before/during chemotherapy.

In a first embodiment of the third aspect, the pharmaceutical composition is applied in an effective dose in the range of 0.1-20, 0.5-15, 0.8-10, 1.0-5, or 1.5-3.5 mg/kg (body weight)/day.

In a second embodiment of the third aspect, the pharmaceutical composition is applied in an effective dose in the range of 1.5-3.5 mg/kg (body weight)/day.

In a third embodiment of the third aspect, the pharmaceutical composition can be further applied simultaneously, that is jointly or separately, or in succession, with medicaments for chemotherapy.

In a fourth embodiment of the third aspect, the medicament for chemotherapy is selected from paclitaxel, albumin-bound paclitaxel, docetaxel, or gemcitabine, or any conventional medicament for chemotherapy which has a side effect of suppressing immunity.

In a fifth embodiment of the third aspect, the pharmaceutical composition is applied at the moment the subject is confirmed suffering from cancers.

In a sixth embodiment of the third aspect, the pharmaceutical composition is applied for at least 28 days, 21 days, 14 days, 7 days, 4 days or 2 days before chemotherapy.

In a seventh embodiment of the third aspect, the pharmaceutical composition is applied every day during the cycle of chemotherapy. It is a further embodiment of the present invention that this invention is applied to a human subject.

There is a further embodiment of the third aspect that the pharmaceutical composition of the present invention is applied to the subject being confirmed of suffering from cancers for at least 28 days, 21 days, 14 days, 7 days, 4 days or 2 days before chemotherapy and during the cycle of chemotherapy.

In yet another embodiment of the presently claimed invention, the pharmaceutical composition is applied daily while the chemotherapeutic agent for chemotherapy is applied weekly to a subject in need thereof. The daily effective dose of the pharmaceutical composition is about 3.3 mg/kg while the weekly effective dose of the chemotherapeutic agent is about 1.6 mg/kg. In that embodiment, the subject is human and route of administration of the chemotherapeutic agent is via intraperitoneal (i.p.) injection. In that embodiment, the pharmaceutical composition is administered orally daily for at least a week before the chemotherapeutic agent is administered via i.p. injection on the last day of the first week of the oral administration of the pharmaceutical composition. The pharmaceutical composition of the present invention comprises at least one polysaccharide from *Radix Astragali* extract, *Radix Codonopsis* extract, *Ganoderma sinense* extract, or a mixture thereof. The chemotherapeutic agent comprises paclitaxel, albumin-bound paclitaxel, docetaxel, and gemcitabine. The subject being administered with the combination of said pharmaceutical composition and chemotherapeutic agent is human who suffers from mammary cancer.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

Figure 1:
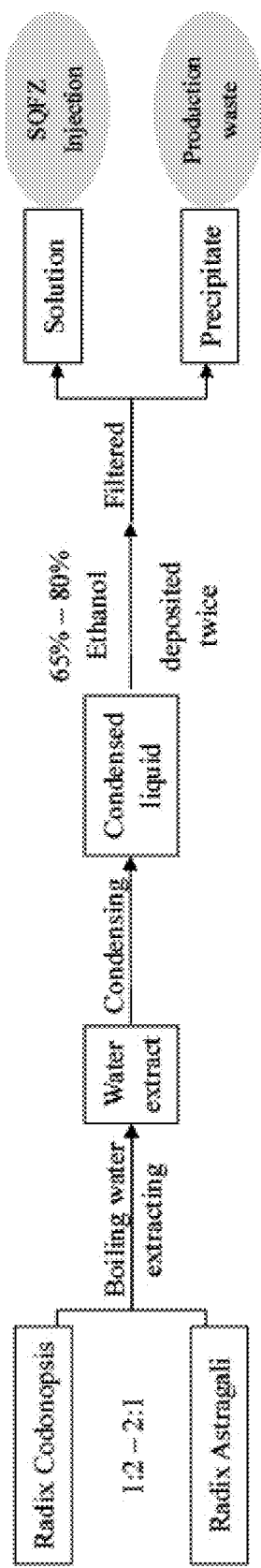
FIG. 1 shows the production protocol of SQFZ Injection.

The present invention is not to be limited in scope by any of the specific embodiments described herein. The following embodiments are presented for exemplification only.

In the first aspect, the invention provides a pharmaceutical composition for modulating the immune system comprising at least one polysaccharide extracted from *Radix Astragali, Radix Codonopsis, Ganoderma sinense*, or mixtures thereof. In particular, the polysaccharides have molecular weight in the range of 500-2,500 kDa, preferably 600-2,000 kDa and more preferably 700-1,900 kDa.

The polysaccharides have hyperbranched structures and are bound to a protein, with a protein content ranging from 1-20%, more preferably in the range of 5-15%.

The polysaccharides comprise constituents selected from the group of glucose, galactose, mannose, rhamnose, arabinose, their dextrorotary and levorotary compounds, and combinations thereof.

Preferably, the polysaccharides comprise essentially glucose, galactose and mannose as constituents with any two constituents in the molar ratio ranging from 1:30 to 30:1, 1:20 to 20:1, or 1:10 to 10:1.

The polysaccharide comprises at least one sugar residue selecting from the group consisting of 1,2,4-linked Rhap, α-1,4-linked Glcp, α-1,4-linked GalAp6Me, β-1,3,6-linked Galp, α-T-Araf, α-1,5-linked Araf, T-linked Araf, T-linked Glcp, T-linked Galp, (1→6)-linked-β-D-glucopyranosyl, (1→4)-linked-β-D-glucopyranosyl, (1→3)-linked-β-D-glucopyranosyl, non-reducing end β-D-glucopyranosyl, t-, 1,3-, 1,4-, 1,6-, 1,3,4- and 1,3,6-linked Glcp, t-linked Galp, 1,6-linked Manp, and combinations thereof.

In an embodiment of the invention, the polysaccharide is extracted from *Ganoderma sinense*. An example of the polysaccharides is defined by NMR spectra of FIGS. 5A and 5B, with an apparent molecular weight of 830 kDa and about 6.8% protein content. Such polysaccharide presents a linear molecular structure and comprises mannose, glucose and galactose as constituents in the molar ratio of 4.7:27.1:1.0. Another example of the polysaccharides is defined by NMR spectra of FIGS. 6A and 6B, with an apparent molecular weight of 1860 kDa and about 10.13% protein content. Such polysaccharide has a hyperbranched 1,6-glcp backbone structure, comprising mainly glucose and trace amounts of galactose and mannose as constituents, with (1→3)-linked glucosyl and (1→4)-linked glucosyl branches at O-3 position.

In another embodiment of the invention, the polysaccharides are extracted from *Radix Astragali*. An example of such polysaccharides has a molecular weight of 1,334 kDa and low protein content (only 0.72%). It comprises rhamnose, arabinose, glucose, galactose, galacturonic acid, as constituents in a molar ratio of 0.03:1.00:0.27:0.36:0.30. Such polysaccharide is characterized by NMR spectra of FIGS. 7A and 7B.

The pharmaceutical composition according to the present invention may be optionally added with one or more pharmaceutically acceptable auxiliaries, such as diluents, excipients, fillers, binders, wetting agents, anti-foaming agents, disintegrators, sorbefacients, surfactants, adsorption carriers, lubricants etc. These auxiliaries are known in the art and commercially available. The amount of suitable auxiliaries can be determined by trials by those skilled in the art.

The pharmaceutical composition according to the present invention can be formulated in the form of injection, tablet, pill, capsule, powder, water-dispersible powder, granule, water-dispersible granule, paste, solution, suspension, emulsion, aerosol for inhalation. Preferable, the pharmaceutical composition is formulated as tablet, pill, capsule, and granule.

In another aspect, the present invention provides a process of extracting polysaccharides from *Radix Astragali, Radix Codonopsis* or *Ganoderma sinense*, characterized in that one or more solid/liquid extractions are carried out. The liquid extract is precipitated with an organic solvent, centrifuged and filtered, and then the precipitate is subsequently dried so as to yield crude polysaccharides.

The crude polysaccharides were further purified by ion-exchange chromatography followed by gel-permeation chromatography (GPC). Preferred eluents include water, bases such as sodium hydroxide, and salt solutions such as sodium chloride solution.

In one embodiment of this method, the extraction(s) is (are) carried out with boiling water. Preferably, the organic solvent used is ethanol.

Another aspect of the present invention is a method of modulating immune system by applying said pharmaceutical composition. The polysaccharides according to the present invention exhibit significant immunomodulating effects by stimulating the proliferation of human peripheral blood mononuclear cells (PBMCs) and enhancing its interleukin production.

The present invention also provides a pharmaceutical composition comprising at least one polysaccharide as defined above extracted from *Radix Astragali, Radix Codonopsis, Ganoderma sinense*, or mixtures thereof, for preventing and/or pretreating and/or treating cancers.

The pharmaceutical composition according to the present invention is applied through enteral or parenteral administration. In particular, the pharmaceutical composition is applied by injection, inhalation, oral or topical administration. The pharmaceutical composition is preferably applied through oral administration.

The effective dose of the pharmaceutical composition is in the mass range of 0.1-20, 0.5-15, 0.8-10, 1.0-5, or 1.5-3.5 mg/kg (body weight)/day. Preferably, the mass range of effective dose of the pharmaceutical composition is 1.5-3.5 mg/kg (body weight)/day. In some embodiments, the pharmaceutical composition is applied every day. In an exemplary embodiment of the presently claimed invention, the effective dose of the pharmaceutical composition is about 3.3 mg/kg/day.

The pharmaceutical composition is for use in preventing and/or pretreating and/or treating cancers, for example but not limited to, mammary, lung, liver, prostate, bladder, bone, bowel, colon, rectal, cervical, pancreatic, ovarian, skin, stomach, penis cancer, etc.

The pharmaceutical composition according to the present invention can be further applied simultaneously, that is jointly or separately, or in succession, with medicaments for chemotherapy, whereas the sequence, in the case of separate application, generally does not have any effect on the result of the control measures.

Suitable medicaments for chemotherapy are any chemical applied in a treatment which has a side effect of suppressing immunity. Examples include paclitaxel (sold under the trademark TAXOL® by Bristol-Myers Squibb), albumin-bound paclitaxel (sold as ABRAXANE® by Celgene Corporation), docetaxel (marketed under the name of TAXOTERE® by Sanofi-Aventis), and gemcitabine (marketed as GEMZAR® by Eli Lilly and Company).

In one embodiment, the pharmaceutical composition is applied a period before chemotherapy. The application period prior to chemotherapy depends on the medicament used in chemotherapy, and target disease. Preferably, the pharmaceutical composition is applied at the moment the subject is confirmed suffering from cancers. The pharmaceutical composition is preferably applied for at least 28 days, 21 days, 14 days, 7 days, 4 days or 2 days before chemotherapy.

In another embodiment, the pharmaceutical composition is applied in combination with medicaments for chemotherapy. In particular, the pharmaceutical composition is applied during the whole cycle of chemotherapy. In some embodiments, the pharmaceutical composition is applied every day during the cycle of chemotherapy.

In an exemplary embodiment of the presently claimed invention, the pharmaceutical composition is applied daily while the chemotherapeutic agent for chemotherapy is applied weekly to a subject in need thereof. The daily effective dose of the pharmaceutical composition is about 3.3 mg/kg while the weekly effective dose of the chemotherapeutic agent is about 1.6 mg/kg. In that embodiment, the subject is human and route of administration of both the pharmaceutical composition and the chemotherapeutic agent is via intraperitoneal (i.p.) injection. In that embodiment, the pharmaceutical composition is administered via i.p. injection daily for at least a week before the chemotherapeutic agent is administered via i.p. injection on the last day of the first week of the i.p. injection of the pharmaceutical composition, i.e., the pharmaceutical composition is administered daily for six consecutive days before administering the chemotherapeutic agent. The pharmaceutical composition of the present invention comprises at least one polysaccharide from *Radix Astragali* extract, *Radix Codonopsis* extract, *Ganoderma sinense* extract, or a mixture thereof. The chemotherapeutic agent comprises paclitaxel, albumin-bound paclitaxel, docetaxel, and gemcitabine.

The following examples illustrate the invention without limiting it in any way.

Example 1

Extraction of Polysaccharides from *Ganoderma sinense*

Dried fruiting bodies of *Ganoderma sinense* (1 kg) were extracted with distilled water (12 L×2) at 100° C. for 1 hour. The combined water extracts were concentrated to 300 mL under a reduced pressure and then centrifuged. The supernatant was collected, to which 1.2 L of 95% ethanol was added slowly by stirring, and then kept at 4° C. overnight. The precipitate were obtained by centrifugation, then completely dissolved in appropriate volume of distilled water and intensively dialyzed for two days (cut-off Mw 7000 Da). The retentate was concentrated and the protein was removed using Sevage reagent ($CHCl_3$: BuOH=4:1, v/v, 15 min×7). Finally, the extracts were centrifuged and the supernatant was freeze-dried to yield the crude polysaccharides (2.7 g).

Example 2

Extraction of Polysaccharides from *Radix Astragali*

The air-dried *Radix Astragali* (100 g) was cut into pieces and extracted twice with 1.2 L boiling water for 1 hour. The solution was filtered and concentrated under reduced pressure. The solution was precipitated with four volumes of absolute ethanol for 12 hours. The precipitate was resolved again in water and deproteinized using Sevag method for five times. Then the solution was dialyzed against distilled water for 72 hours. Finally, the retentate was lyophilized with Virtis Freeze Dryer (The VirTis Company, New York, USA) to yield crude polysaccharide (1.67 g).

Example 3

Purification of Polysaccharide Extract by Chromatography

Figure 2:
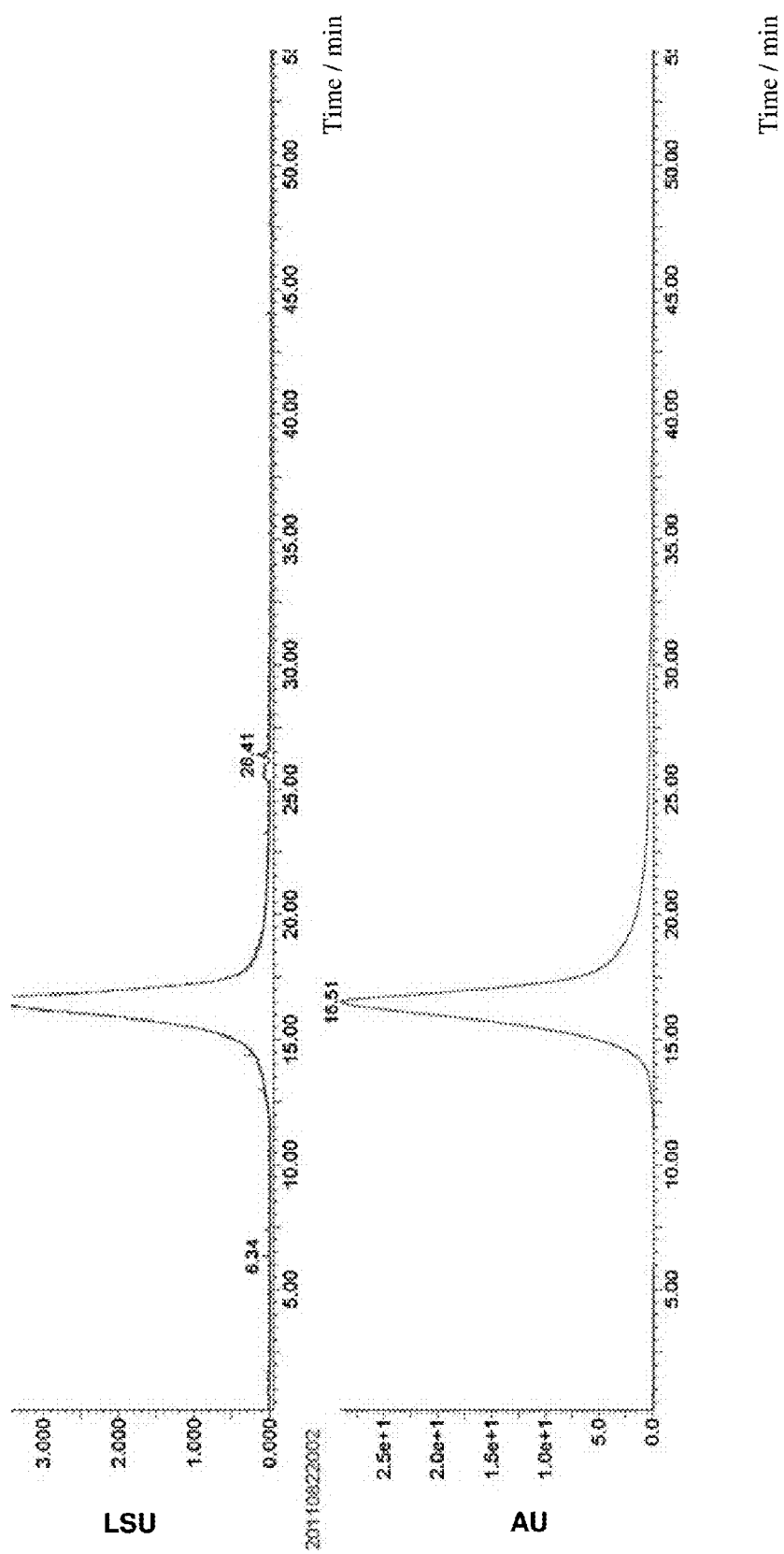
FIG. 2 shows the GPC chromatogram of Example 3.

The crude polysaccharides (2.2 g) from Example 1 was subjected to a DEAE Sepharose CL-6B column (5.0×70.0 cm) and eluted first with $H_2O$ and then stepwise with 0.1 M, 0.3 M, 0.5 M, 1.0 M and 0.2 M sodium hydroxide (NaCl), successively, to give 6 subfractions (Fr.1-6). Fractions of 15 mL were collected and monitored by phenol-$H_2SO_4$ method and UV absorbance at 280 nm Each fraction was dialyzed and lyophilized. The most abundant fraction Fr.4 was further purified by gel-permeation chromatography (GPC) on Sephacryl S-300 and 400 HR (eluting with distilled water) to give the polysaccharide (615 mg). FIG. 2 shows the GPC chromatogram.

Example 4

Purification of Polysaccharide Extract by Chromatography

Figure 3:
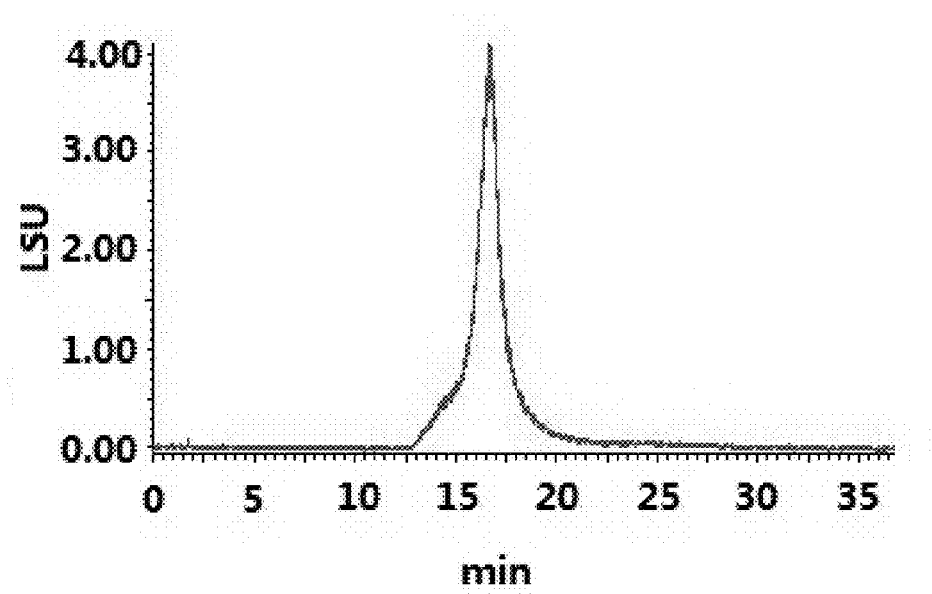
FIG. 3 shows the GPC chromatogram of Example 4.

A portion of the crude polysaccharides (2.2 g) from Example 1 dissolved in water (50 mL), was loaded on a DEAE-Sepharose CL-6B column (5.0×70.0 cm), and eluted with a 6-step gradient with distilled water, 0.1 M sodium chloride (NaCl), 0.3 M NaCl, 0.5 M NaCl, 1.0 M NaCl, and 0.2 M sodium hydroxide (NaOH). The elution was monitored using the phenol-sulfuric acid method. The 0.2 M NaOH fraction was collected as a major fraction, neutralized by 0.2M hydrochloric acid, dialyzed, lyophilized, and purified by gel-permeation chromatography on Sephacryl S-300 and 400 HR eluting with water, to afford a purified polysaccharide. FIG. 3 shows the GPC chromatogram.

Example 5

Purification of Polysaccharide Extract by Chromatography

Figure 4:
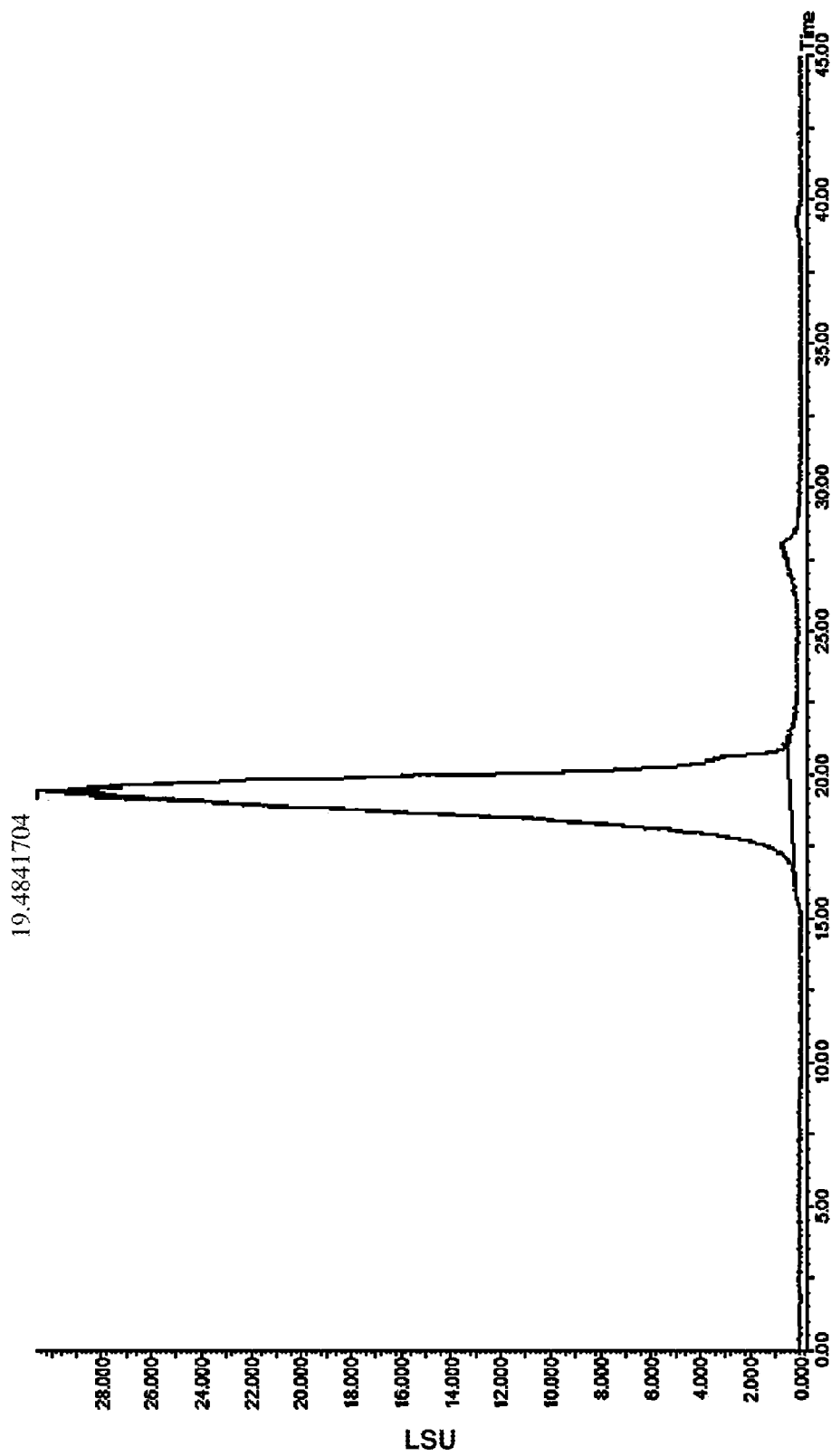
FIG. 4 shows the GPC chromatogram of Example 5.

The crude polysaccharide from Example 2 was dissolved in distilled water (4 mg/mL), filtered through a 0.45 μm membrane and separated by the Buchi Purifier system (BUCHI Labortechnik AG, Switzerland) coupled with a Hiload 26/60 Superdex-200 (2.6×60 cm) column, eluted with water at a flow rate of 2 mL/min. Fractions were collected every 3 minutes and checked using phenol-$H_2SO_4$ under UV detection at 490 nm GPC was used to test the homogeneity of the purified polysaccharide. FIG. 4 shows the GPC chromatogram.

Example 6

Characterization of Polysaccharides by Monosaccharide Composition Analysis

The polysaccharides of Example 3 and 4 (10 mg) were separately hydrolyzed with 2 M trifluoroacetic acid (TFA) at 100° C. for 3 hours. The monosaccharides were analyzed by GC-MS after completely converted into their acetylated derivation by method of Lawrence and Lyengar. Monosaccharide composition analysis indicated that polysaccharides of Example 3 contained mannose, glucose and galactose in the molecular ratio of 4.7:27.1:1.0, while that of Example 4 was mainly composed of glucose, with trace amounts of galactose and mannose.

Example 7

Characterization of Polysaccharide by Monosaccharide Composition Analysis

The polysaccharide of Example 5 was hydrolyzed with 2 M TFA at 120° C. for 2 hours in a sealed test tube. The acid was removed under reduced pressure by repeated evaporation with methanol, and then the hydrolysate was converted into alditol acetates, based on the publication of Thomas M. Jones and Peter Albersheim, *A gas chromatographic method for the determination of aldose and uronic acid constituents of plant cell wall polysaccharides in Plant* Physiology 1972, 49(6), pp. 926-936. Shimadzu GC/MS-QP2010 equipment (Nishinokyo Kuwabaracho, Kyoto, Japan) was used for the identification and quantification of monosaccharides. The polysaccharide of Example 5 was shown to contain rhamnose, arabinose, glucose, galactose, and galacturonic acid in the molecular ratio of 0.03:1.00:0.27:0.36:0.30.

Example 8

Characterization of Polysaccharide by NMR

Figure 5:
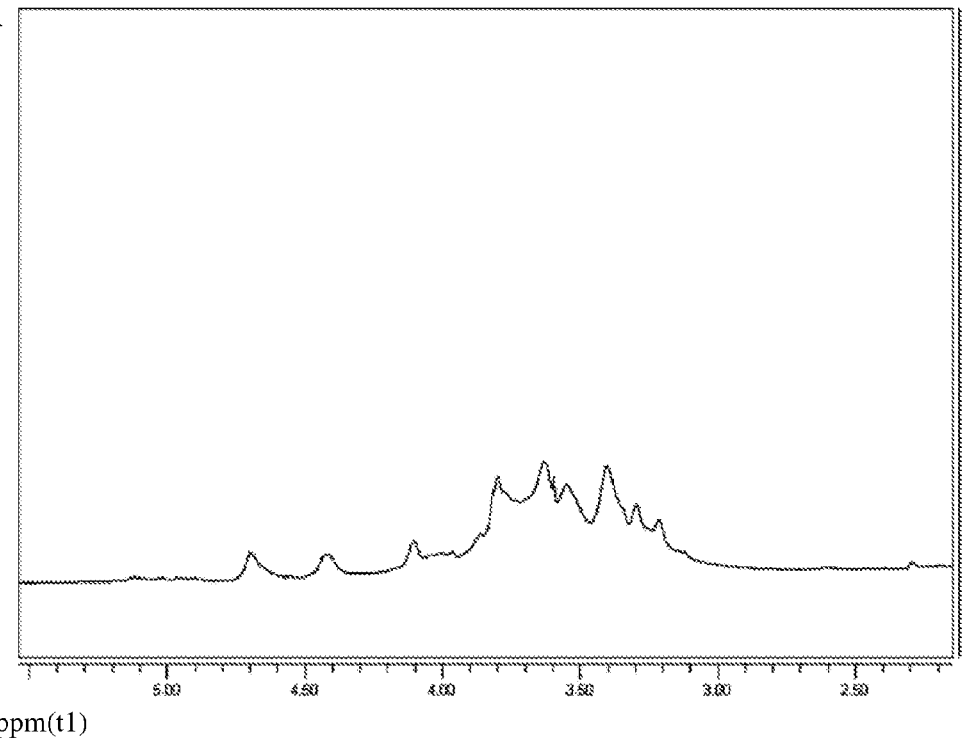
FIG. 5 shows (A) the $^1$H NMR and (B) the $^{13}$C NMR spectra of Example 3.
Figure 5:
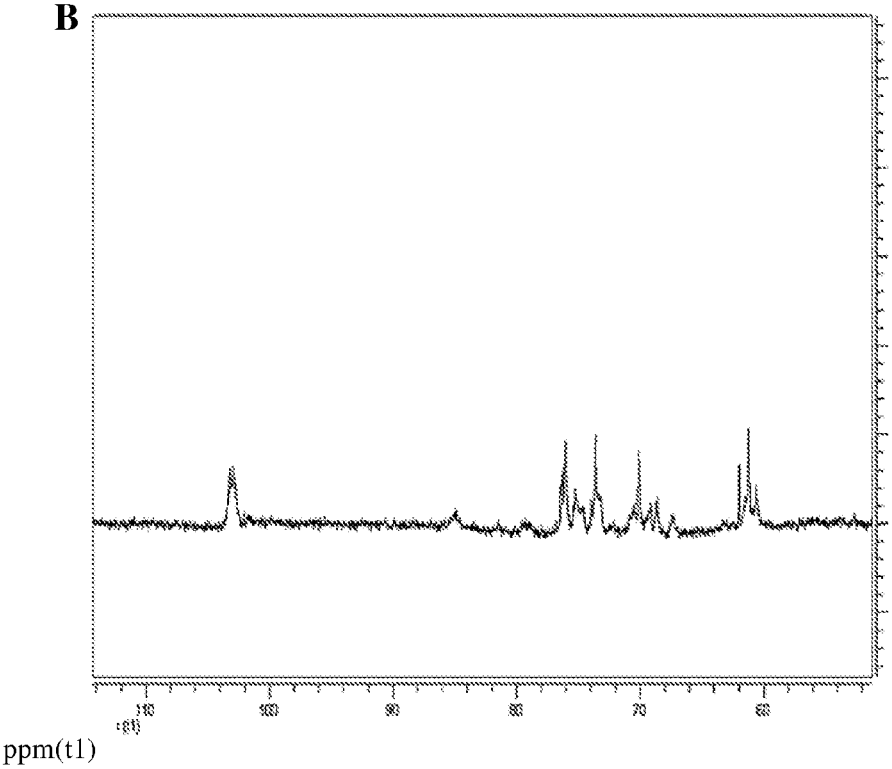
Figure 6:
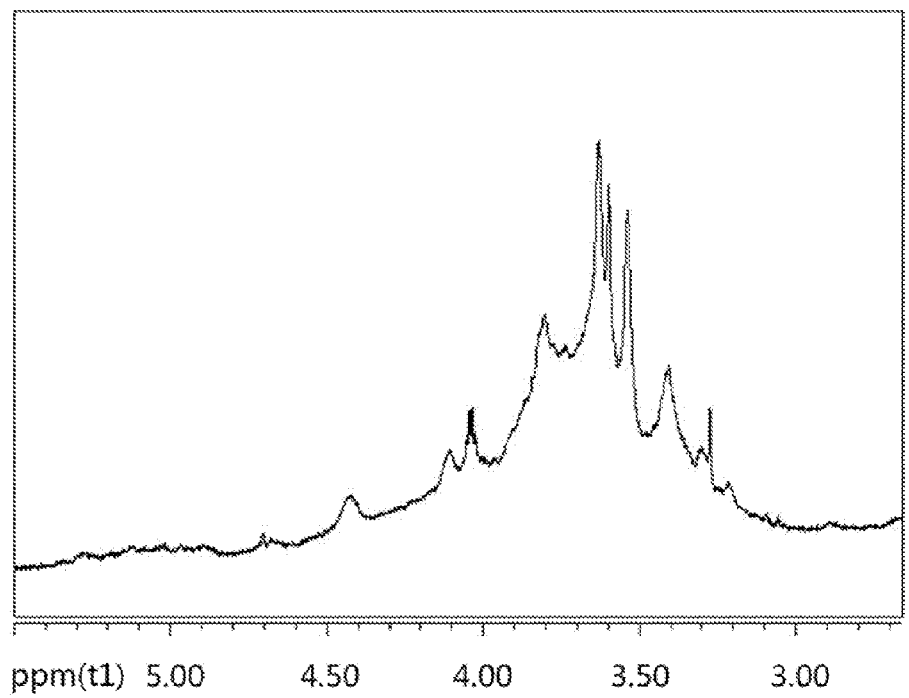
FIG. 6 shows (A) the $^1$H NMR and (B) the $^{13}$C NMR spectra of Example 4.
Figure 6:
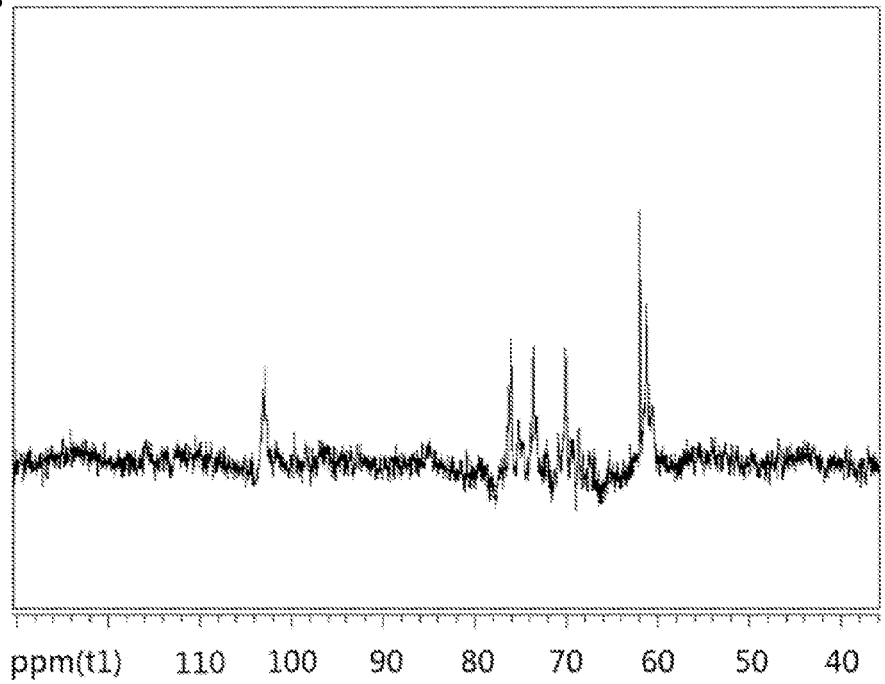
Figure 7:
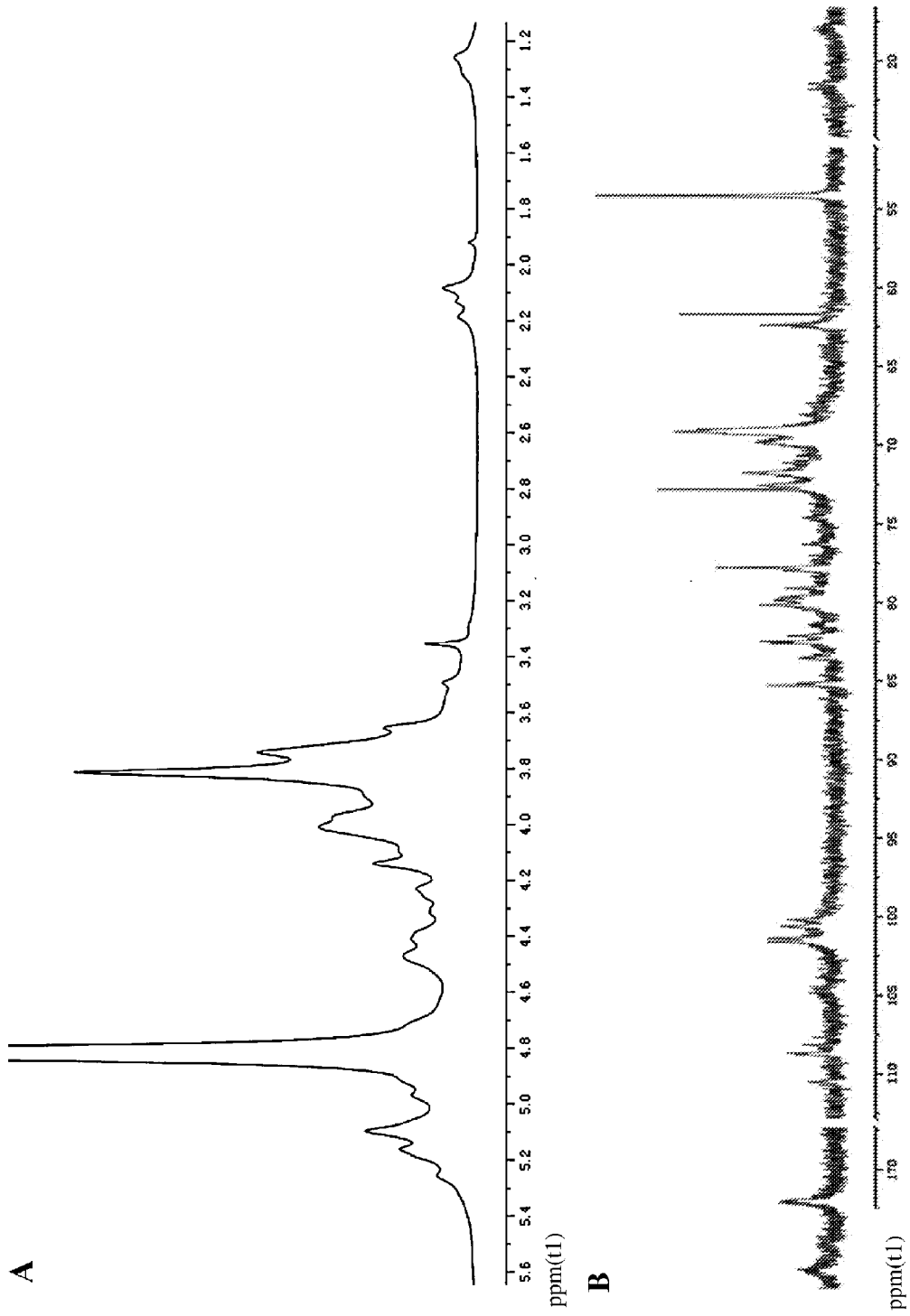
FIG. 7 shows (A) the $^1$H NMR and (B) the $^{13}$C NMR spectra of Example 5.

Polysaccharides of Example 3, 4 and 5 (25 mg) were separately dried in vacuum over $P_2O_5$ for 72 h, and then exchanged with deuterium by lyophilizing with $D_2O$ three times. The deuterium exchanged polysaccharide was put in a 5-mm NMR tube and dissolved in 1.0 mL 99.96% $D_2O$. All NMR spectra were obtained with a Bruker AM 700 spectrometer with a dual probe in the FT mode at room temperature. TMS was used as external standard for the $^{13}$C NMR spectrum, and D$_2$O was used as internal standard for $^1$H NMR spectrum. FIGS. 5-7 illustrate the $^1$H and $^{13}$C NMR spectra of the polysaccharides of Example 3, 4 and 5.

Example 9

Characterization of Polysaccharide by FT-IR

Figure 8A:
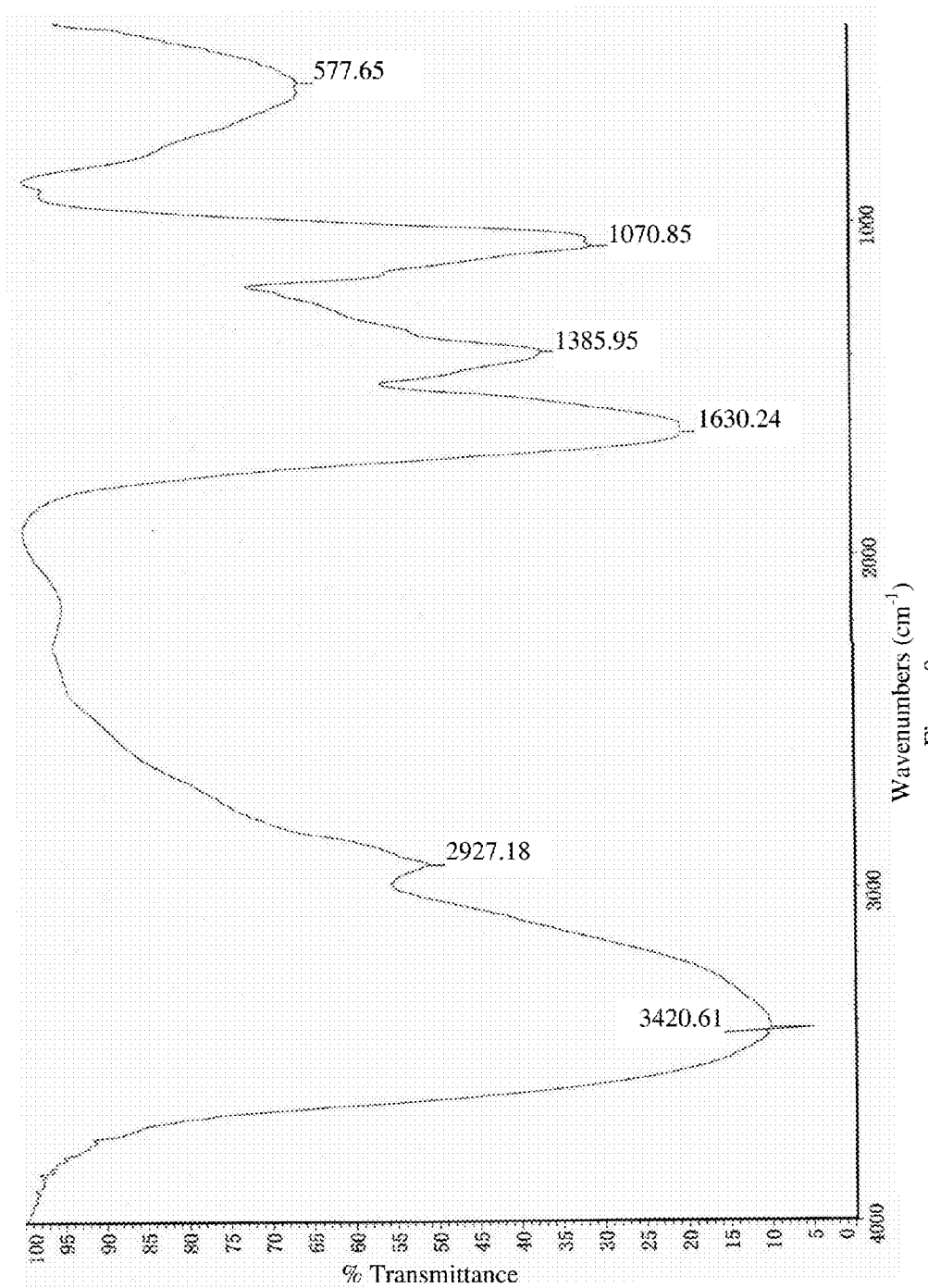
FIGS. 8a, 8b and 8c show the Fourier transform infrared spectra of Example 3, 4 and 5, respectively, recorded in KBr pellets on SPECORD in a range of 400-4000 cm$^{-1}$.
Figure 8B:
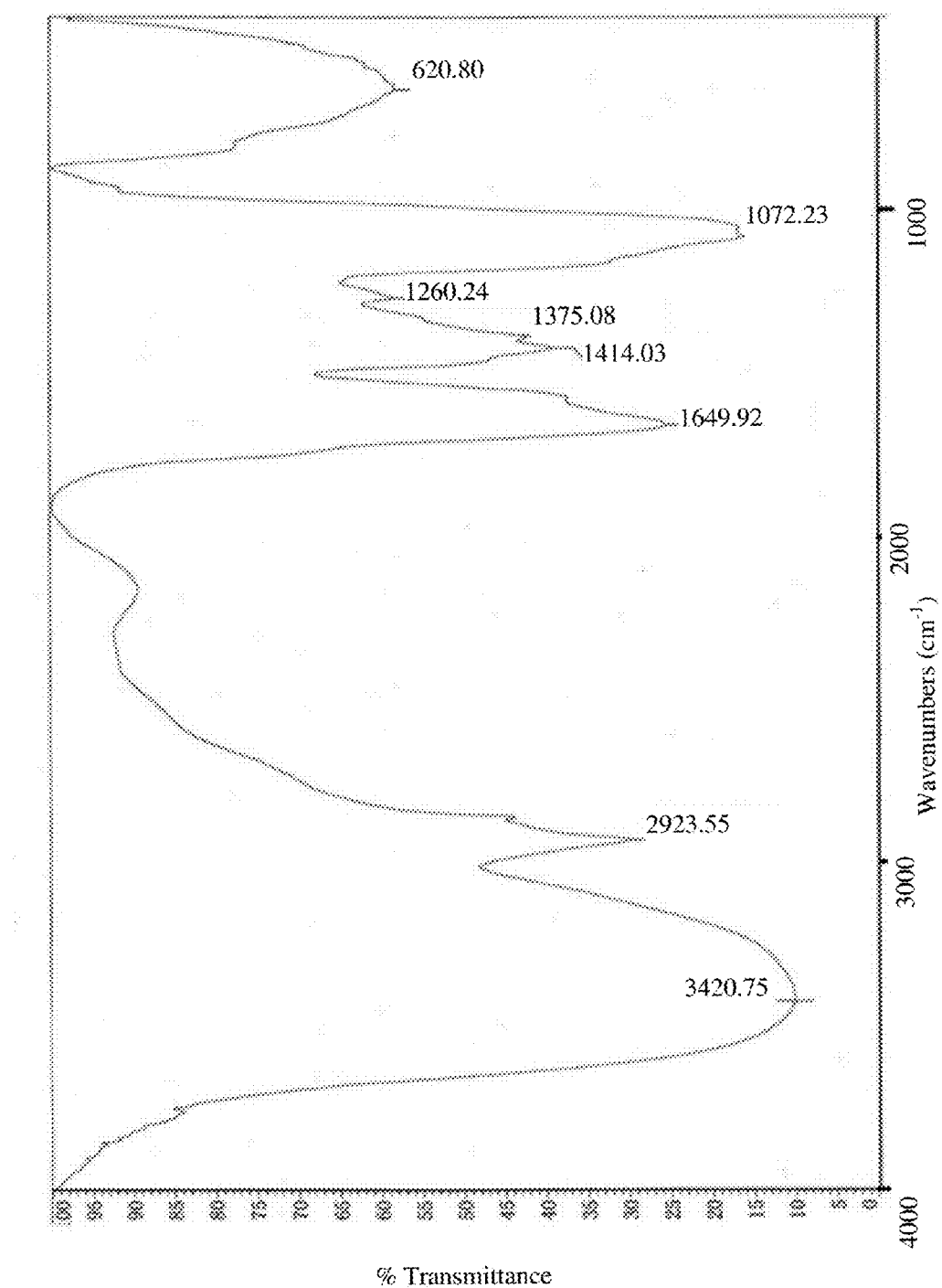
Figure 8C:
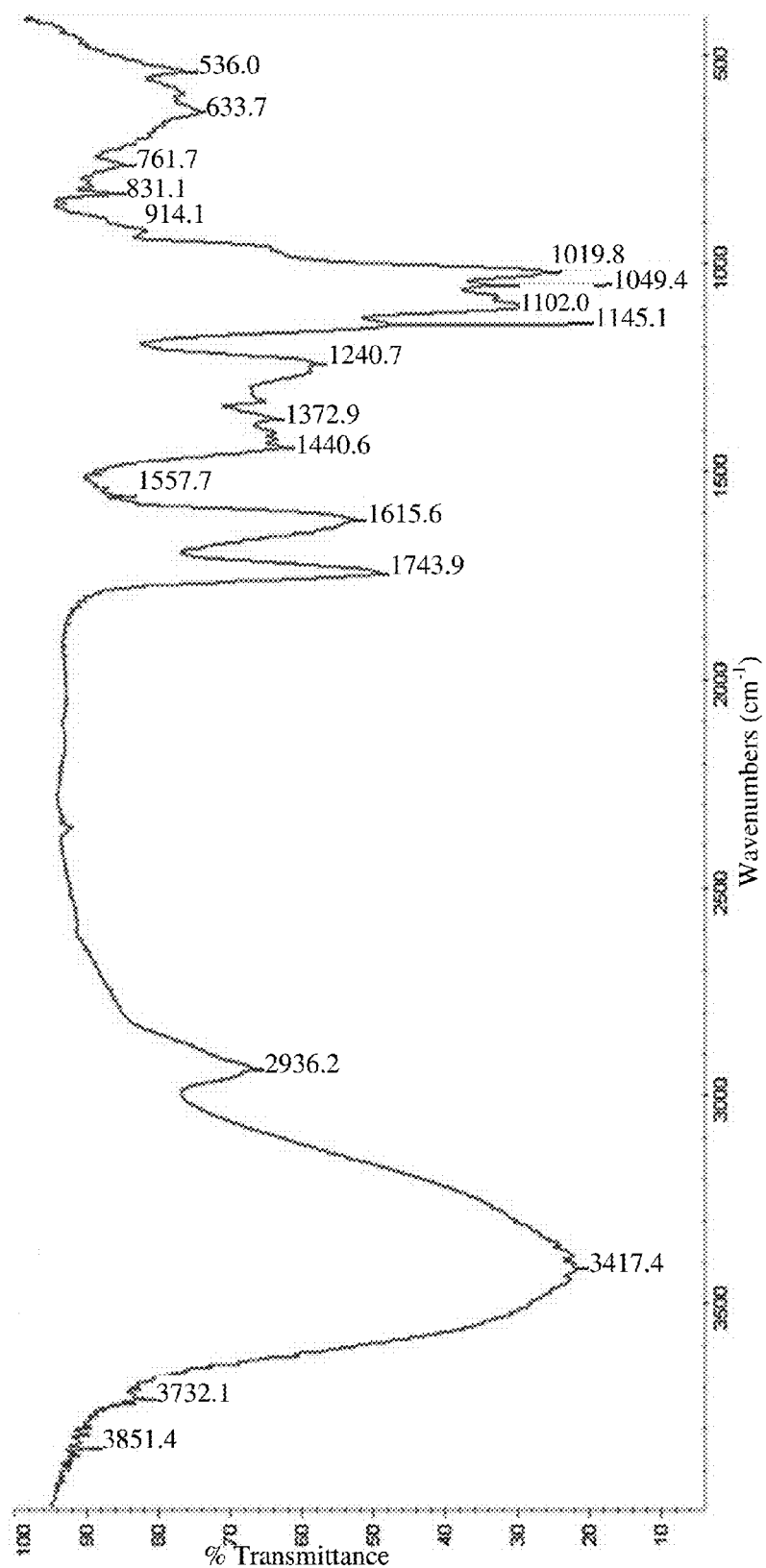
Figure 9A:
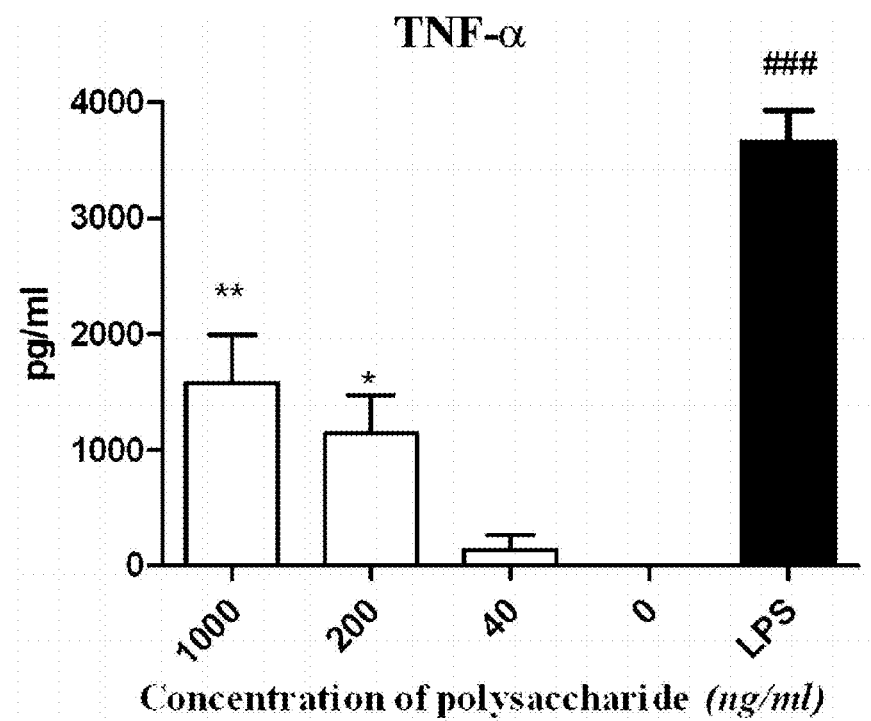
FIGS. 9a-9h show in vitro effects of Example 3 on the cytokine secretion (TNF-α, IL-1β, IL-12, IL-10, GM-CSF, IL-2, IL-4, and INF-γ, respectively) from human PBMC. PMBC (1×10$^6$ cells/mL) were cultured with different concentration of Example 3 (0, 40, 200, 10000, ng/mL) or LPS (8 ng/mL) for 24 hours, and the result were tested by ELISA, n=4 (4 blood sample was employed in this study)
Figure 9B:
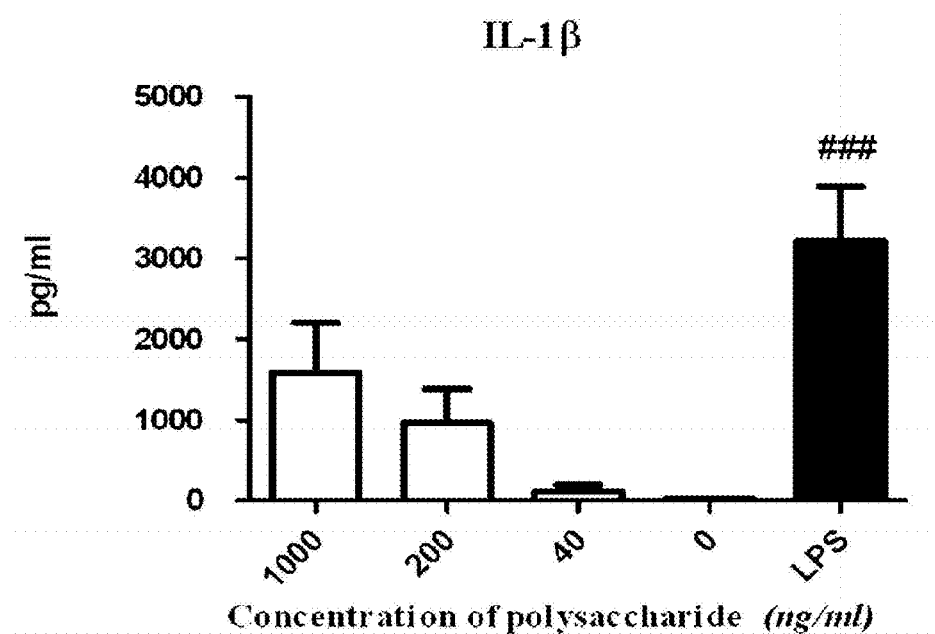
Figure 9C:
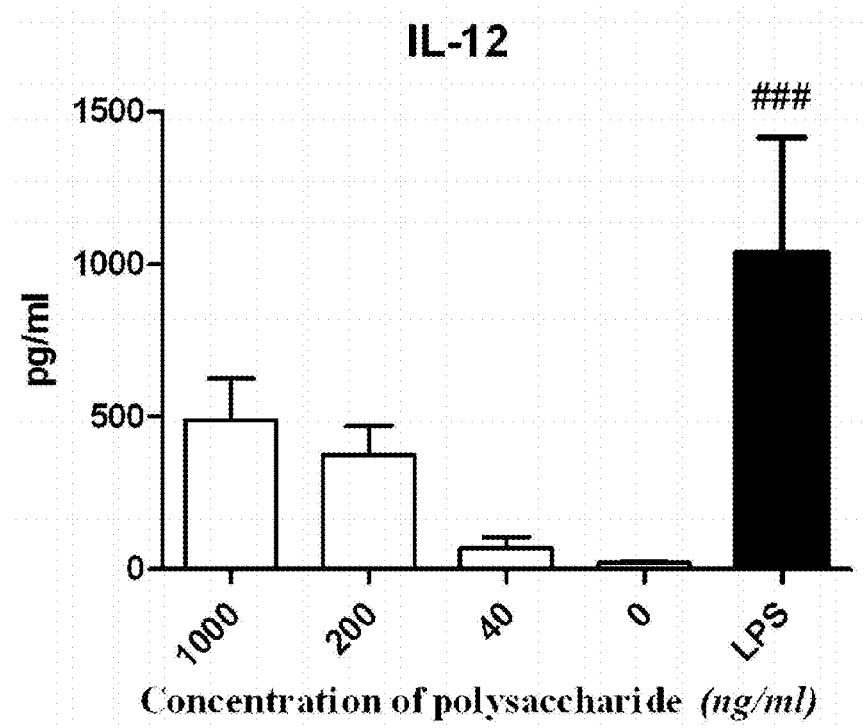
Figure 9D:
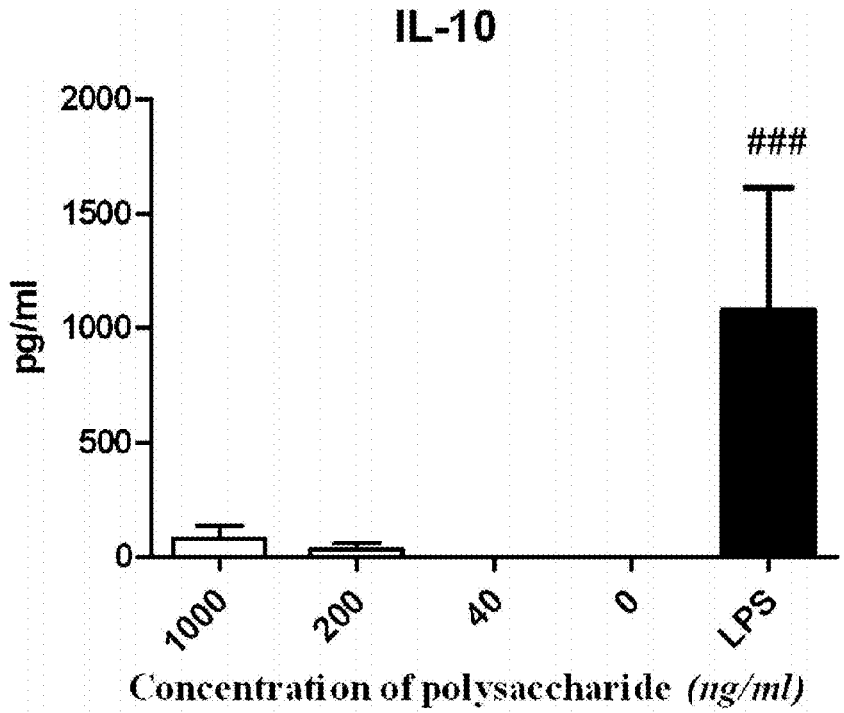
Figure 9E:
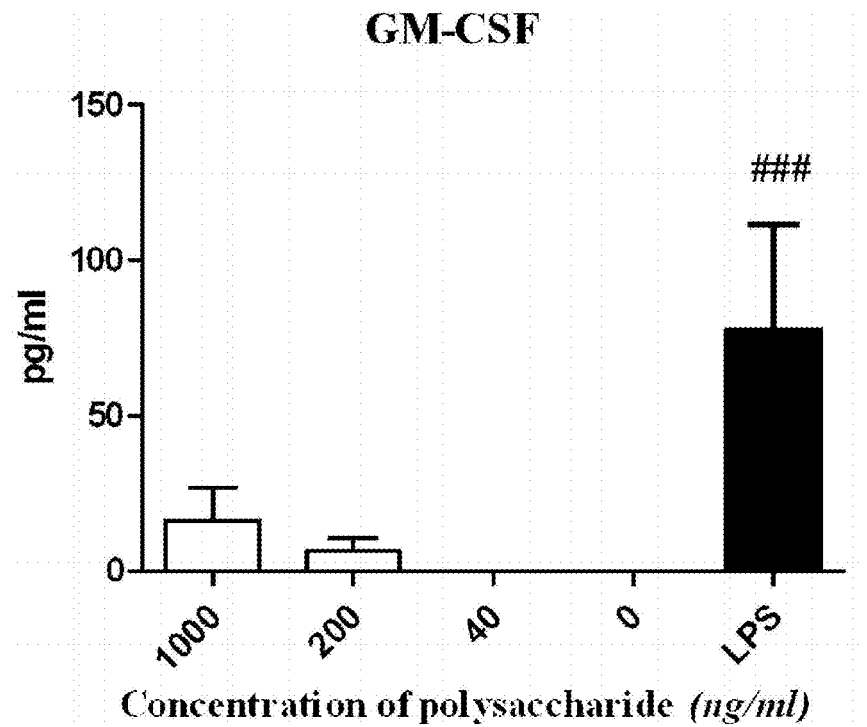
Figure 9F:
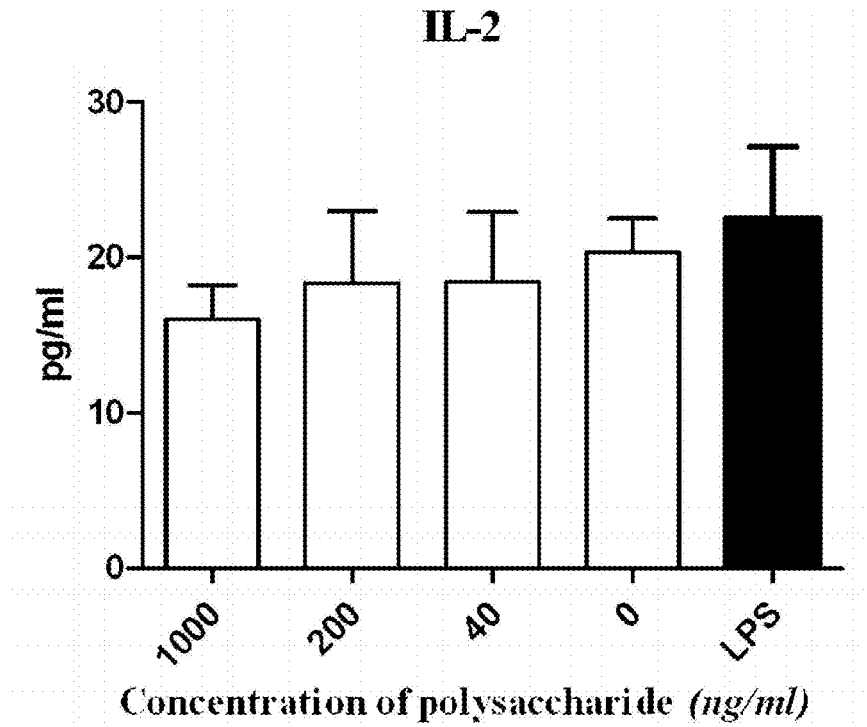
Figure 9G:
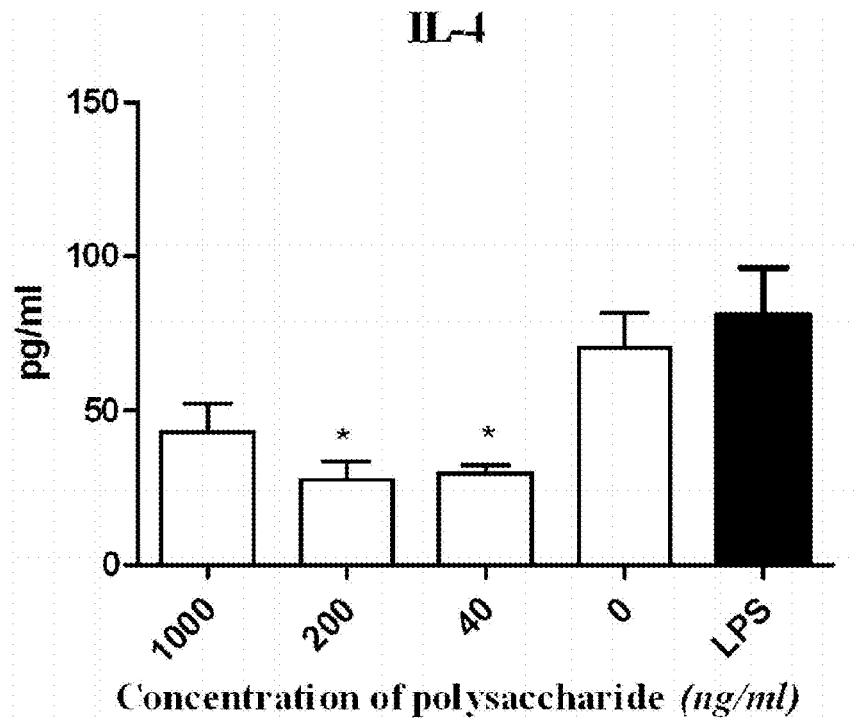
Figure 9H:
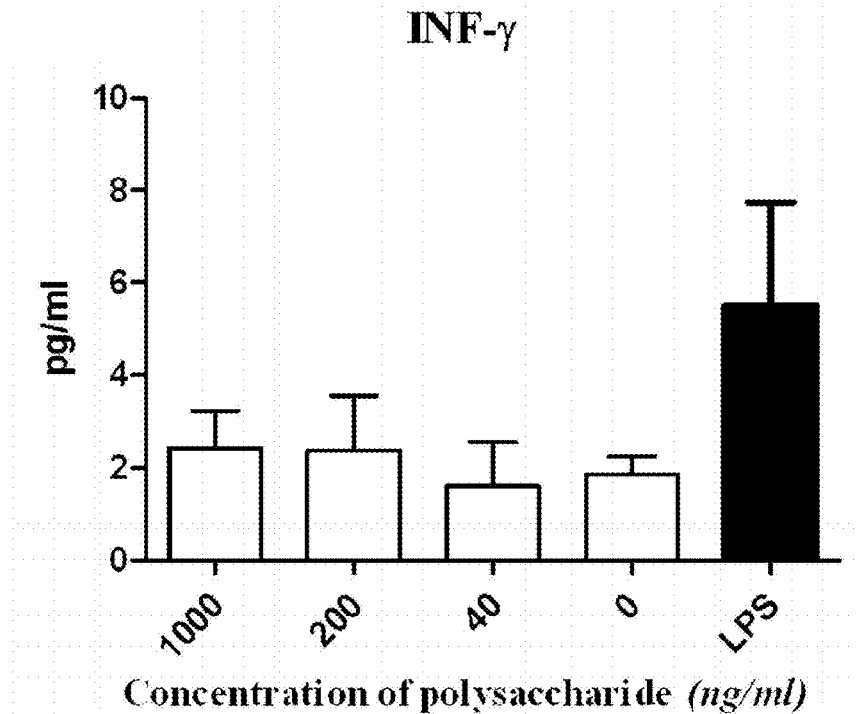

The FT-IR spectra (KBr pellets) of polysaccharides of Example 3, 4 and 5 were recorded on SPECORD in a range of 400-4000 cm$^{-1}$ and shown in FIGS. 8a-8c.

Example 10

In Vitro Immunomodulatory Activity on Human Peripheral Blood Mononuclear Cells (PBMC)

Immunomodulatory activities of the polysaccharides of Example 3, 4 and 5 were determined by the capacity of the compounds to influence the cytokine production by human PBMC. Fresh human buffy coat obtained from 6 healthy adult volunteers (Hong Kong Red Cross Blood Transfusion Service) was diluted with phosphate-buffered saline at a ratio of 1:1. The diluted sample (20 mL) was put in a 50 mL centrifuge tube together with an equal volume of Ficoll-Plaque Plus solution. The tube was then centrifuged at 800 g for 20 min at 18° C. The supernatant was discarded and the PBMCs were resuspended in 4 mL RPMI 1640 medium plus 10% fetal bovine serum (FBS). The cell number was counted and the viability of the cell was checked by trypan blue exclusion assay.

The isolated PBMCs were seeded in a 96-well flat bottom microplate and incubated with the polysaccharides of Example 3, 4, 5, LPS or dextran (0.00003 to 100 μg/mL). After 24 h treatment, concentrations of IL-1β and TNF-α in culture supernatant were determined using ELISA kits (BD Pharmingen Corp., Calif., USA). Polyminxin B (PMB) which is a specific inhibitor of LPS was added in the samples of polysaccharides of Example 3, 4 and 5 in order to exclude the influence of LPS.

Figure 10:
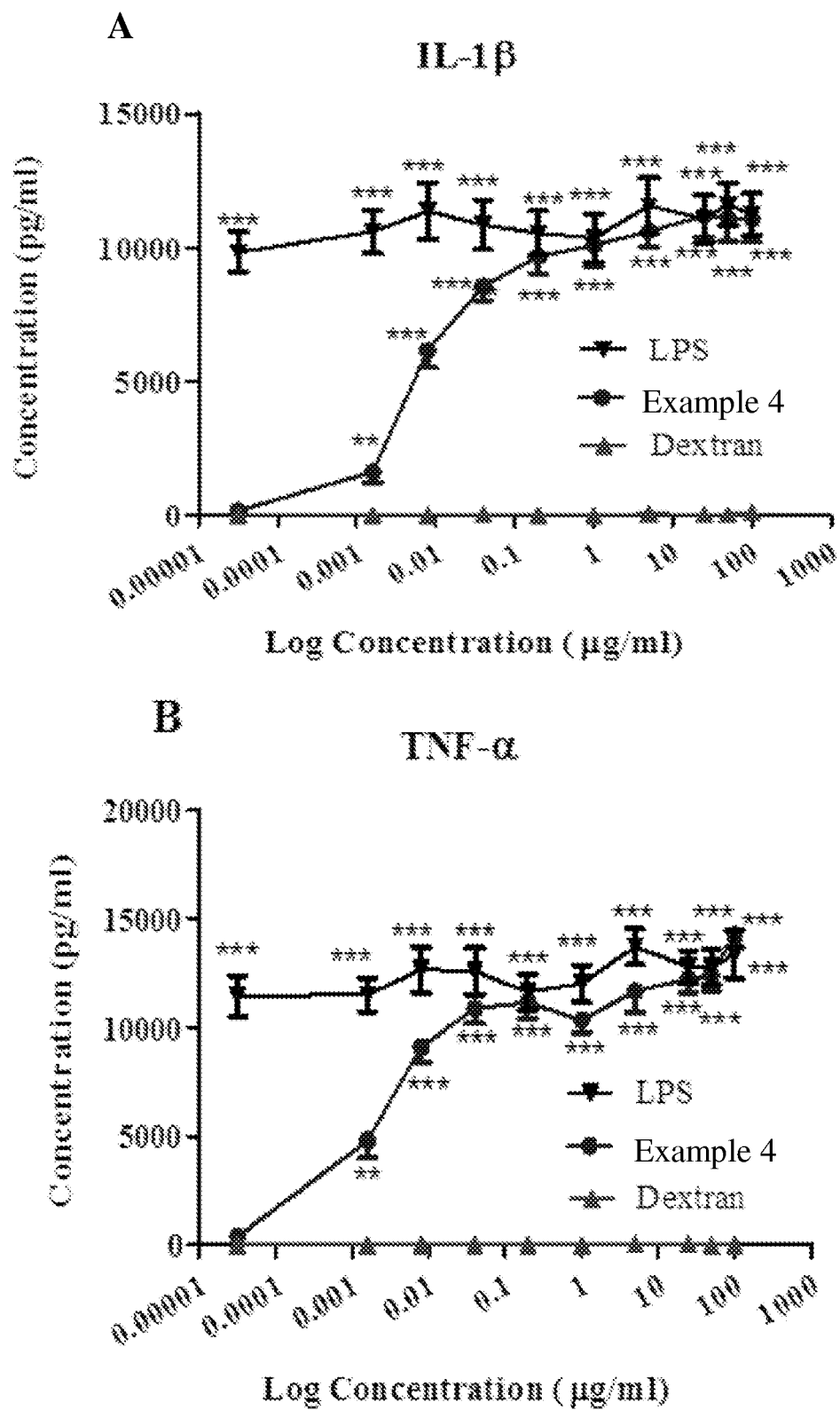
FIG. 10 shows the stimulating effect of Example 4 on the secretion of cytokines (A) IL-1β and (B) TNF-α in PBMCs (n=8). For the assay of cytokine secretion in PBMCs, cells were cultured with different concentrations of Example 4 (0.00003-100 μg/mL) for 48 h, and the release of IL-10 and IL-12 was determined by ELISA, n=8. Dextran and LPS were used as negative and positive control, respectively. Significant differences are indicated by asterisks: *, $p<0.05$; , $p<0.01$; *, $p<0.001$.
Figure 11A:
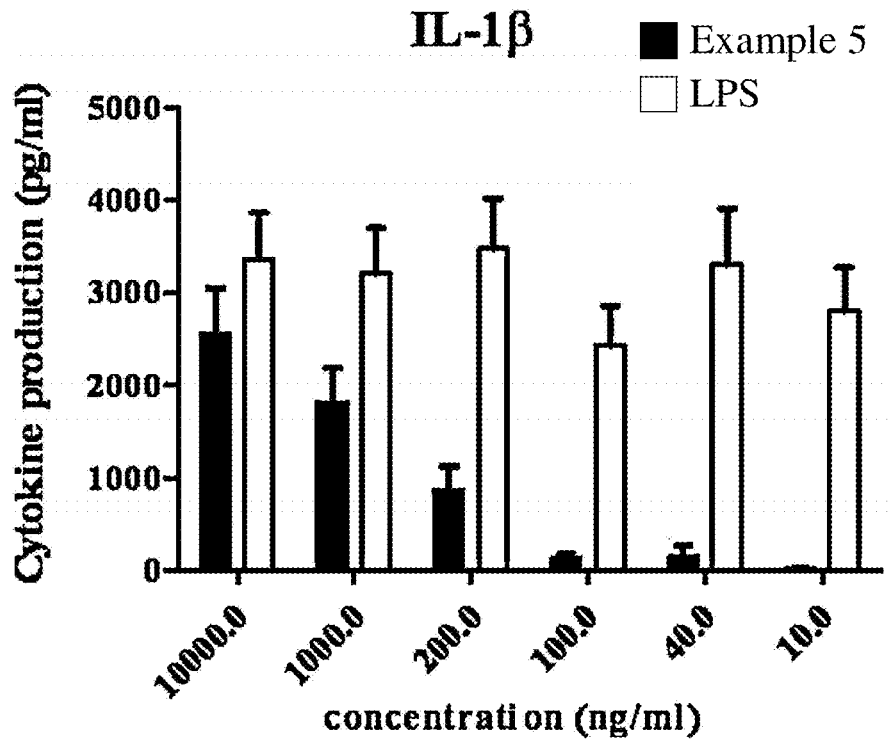
FIGS. 11a-11f show the cytokines production (IL-1β, IL-10, IL-2, IL-12 p40, TNF-α, and GM-CSF, respectively) in PBMCs of Example 4 with the addition of Example 5 or LPS from 2 to 10,000 ng/mL. Each bar represents the mean±SEM of duplicates (n=7)
Figure 11B:
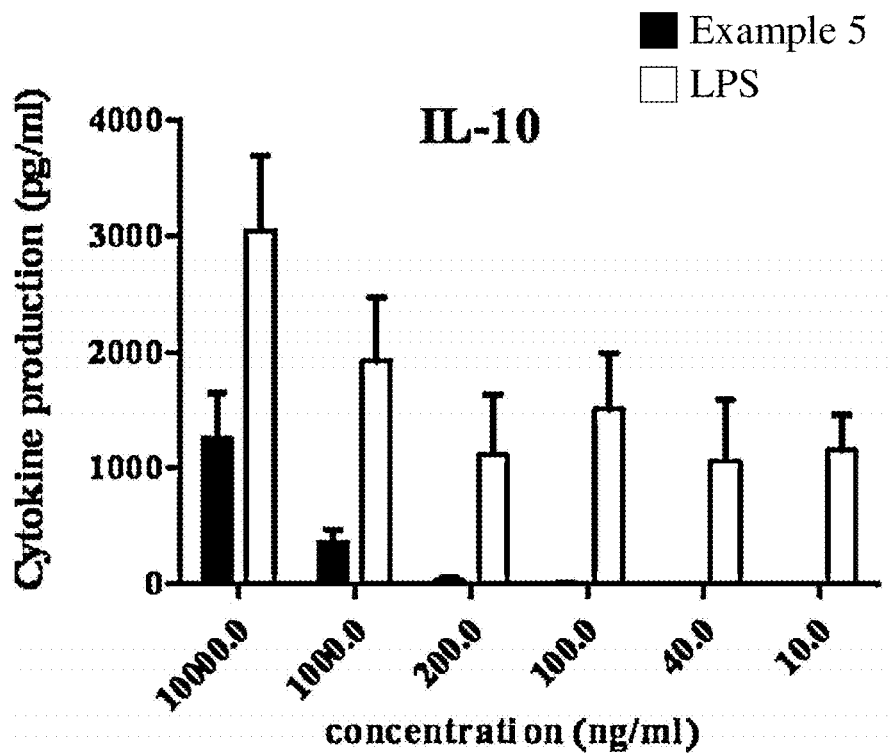
Figure 11C:
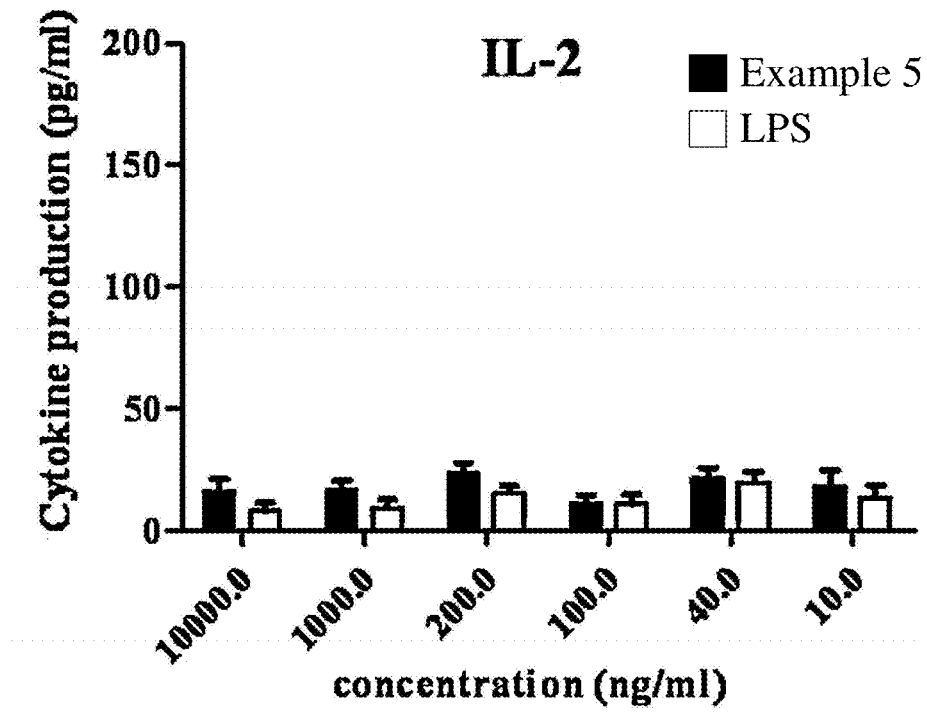
Figure 11D:
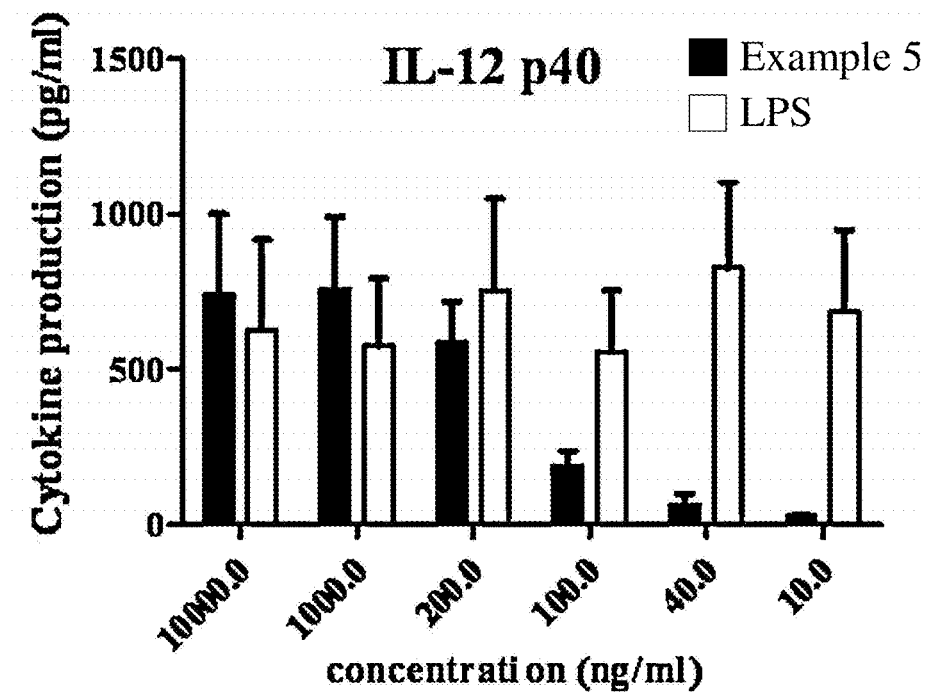
Figure 11E:
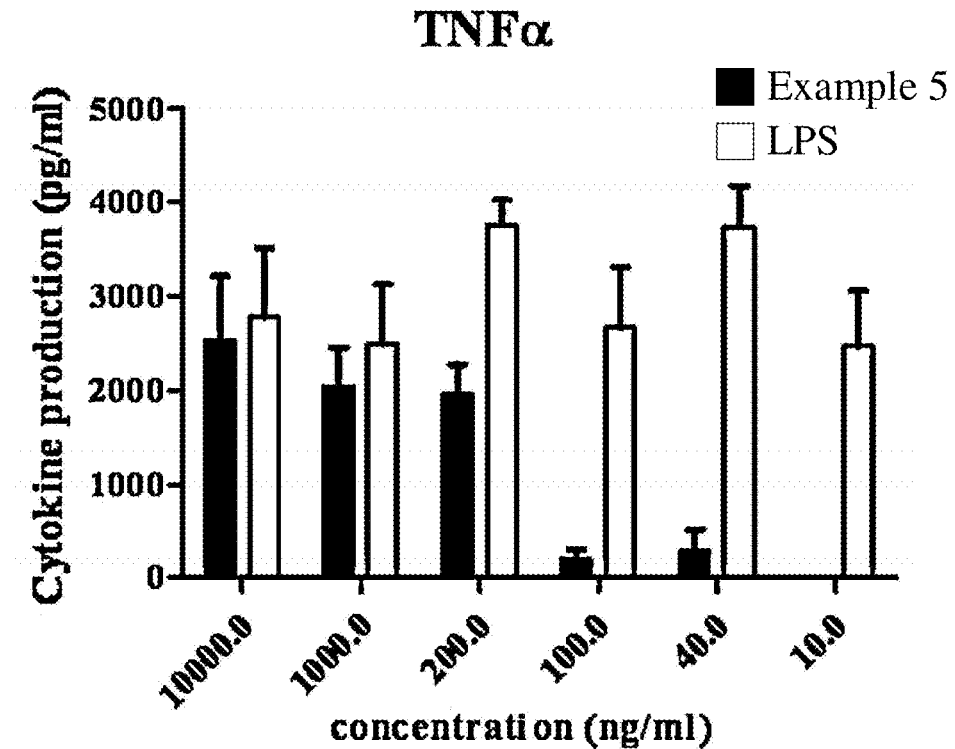
Figure 11F:
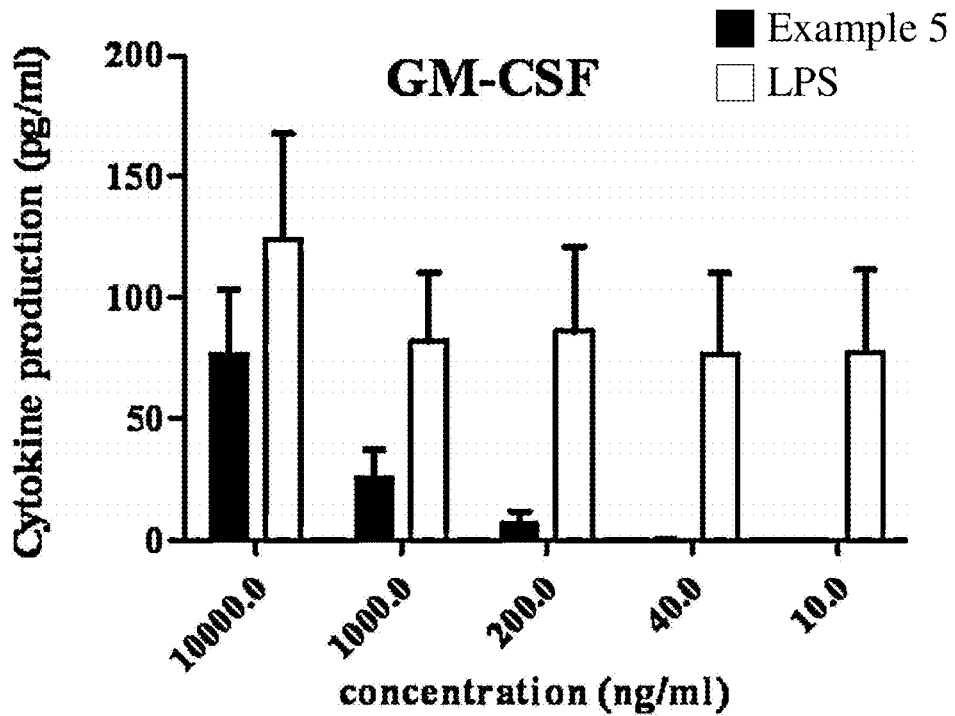

FIGS. 9-11 show the effects of the polysaccharides on the cytokine induction from human PBMCs. The results show that the polysaccharides significantly stimulate the production of cytokine of human PBMCs.

Example 11

Effect on Production of IL-10 and IL-12 in Human Dendritic Cell (DC)

Figure 12:
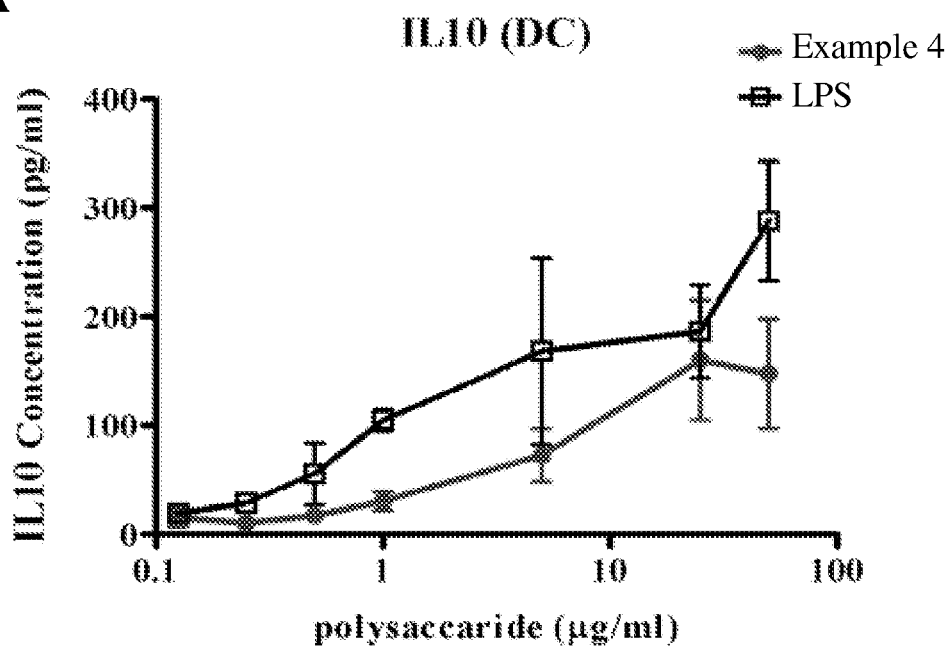
FIG. 12 shows the effect of Example 4 on the induction of (A) IL-10 and (B) IL-12 from human Dendritic Cell (DC)
Figure 12:
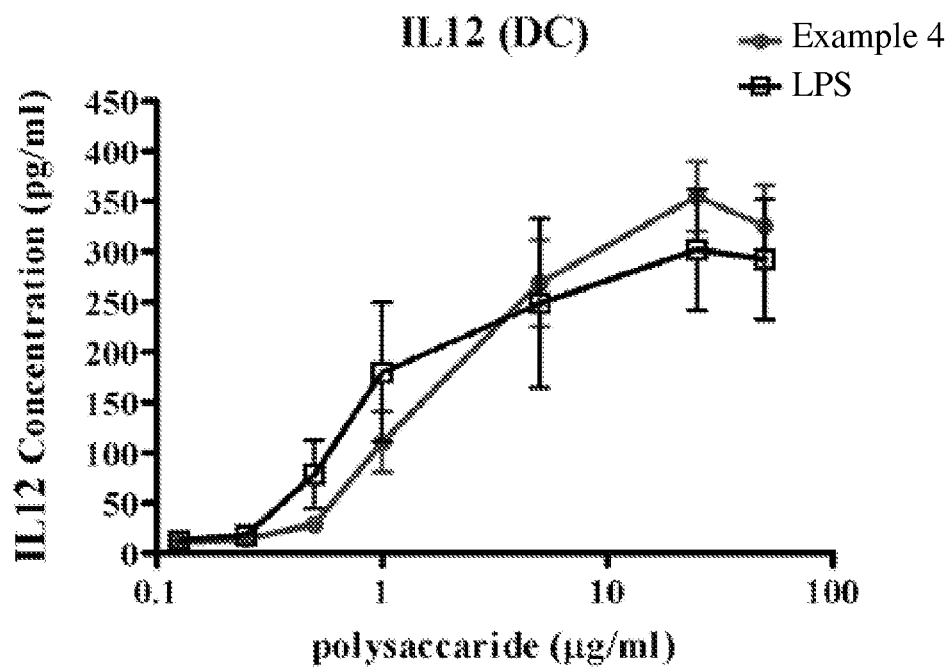

For generation of human monocyte derived dendritic cells (DC) from PBMC, monocytes were positively purified from PBMCs by attachment method. Cells were cultured at 2×10$^6$ cells/mL in RPMI/10% FBS medium supplemented with granulocyte-GM-CSF (50 ng/mL) and IL-4 (40 ng/mL) for 6 days. The immature DC were then harvested and incubated for 2 days by adding Example 4, LPS, or dextran (0.00003-100 μg/mL) Supernatants were collected, and the concentrations of IL-10 and IL-12 were determined by ELISA. FIG. 12 shows that the polysaccharides obtained in Example 4 activate DC by stimulating the secretion of IL-12 and IL-10 from DC.

Example 12

In Vivo Effect on Cytokine Levels on Human PBMCs and Mice Splenocytes

In order to confirm the anti-tumor effects of the polysaccharides obtained in Example 5, the serum levels of multiple anti-inflammatory cytokines were determined using a Bio-Plex Pro Assay mouse multiplex 6 cytokine kit (Bio-Rad Laboratories, Inc., Hercules, Calif., USA), which included granulocyte monocyte colony-stimulating factor, TNF-α, IL-1β, IL-2, IL-10, and IFN-γ, on a Bio-Plex 200 suspension array system (Bio-Rad) equipped with a Bio-Plex manager 6.0 software.

Figure 13:
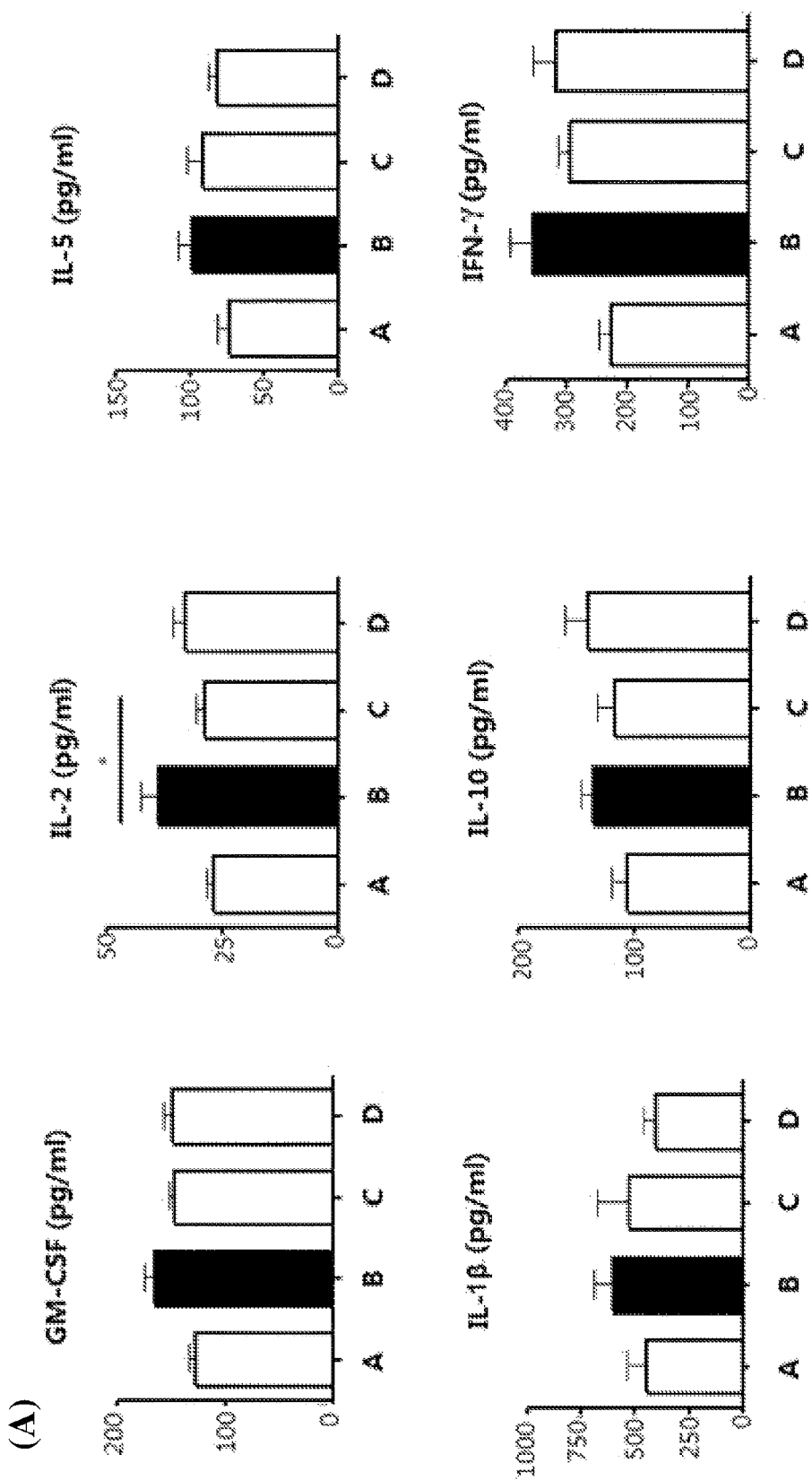
FIG. 13 shows the effects Example 5 on (A) the cytokine levels (Upper row from left to right: GM-CSF, IL-2, IL-5; Lower row from left to right: IL-3β, IL-10, IFN-γ) and (B) the stimulating effect on IL-6, TNF-α, IL-6 and IFN-γ in the splenocytes of the tested mice, wherein the mice were divided into four groups: A. Normal; B. Tumor control; C. treatment; D. pretreatment.

Polysaccharides obtained in Example 5 promote cytokine production of human PBMCs and mice splenocytes (FIGS. 13a and 13b). Compared to those cytotoxic agents, Example 5 itself is not cytotoxic.

Example 13

Therapeutic Effect on BALB/c Mice Orthotopically Injected with 4T1 Mouse Mammary Cancer Cells Female BALB/c mice (6-8 weeks of age) were provided by Laboratory Animal Services Center, The Chinese University of Hong Kong (CUHK), and were housed under pathogen-free conditions, approved by Animal Experimentation Ethics Committee of CUHK. 4T1 cells (4×10$^5$), re-suspended in 0.2 ml phosphate buffered saline (PBS), were subcutaneously (s.c.) inoculated at the mammary fat pad of each mouse. The tumor-bearing mice were randomly divided into three groups (n=10): control group (D$_2$O, oral fed everyday), pretreatment group, and treatment group. Pretreatments of Example 1 and 5 (40 mg/kg/day/mouse) were initiated one week before cancer cell implantation and were continued every day for four weeks. For treatment group, treatments of Example 1 and 5 (40 mg/kg/day/mouse) were initiated after cancer cell implantation and were continued every day for four weeks. Body weight of each mouse was measured once a week during treatment period. At day 28, mice were sacrificed; serum samples were collected for cytokine measurement, and the spleens were removed for in vitro lymphocyte transformation assay.

Figure 14:
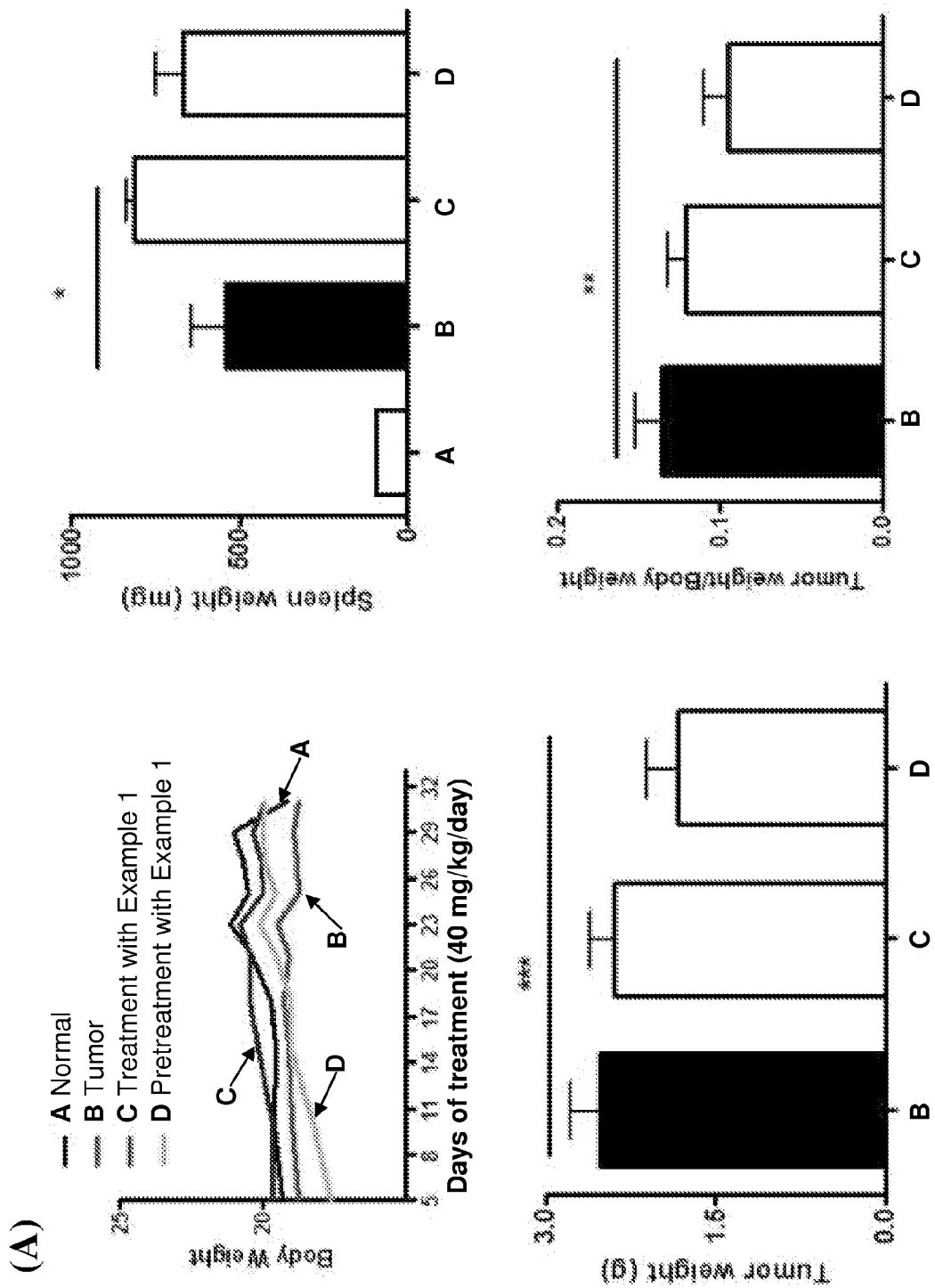
FIG. 14 shows the therapeutic effect of (A) Example 1 and (B) Example 5 on BALB/c mice orthotopically injected with 4T1 mouse mammary cancer cells in terms of the body weight (upper left panel), spleen weight (upper right panel), tumor weight (lower left panel), and tumor/body weight (lower right panel) of the tumor bearing mice. The mice were divided into four groups: A. Normal; B. Tumor control; C. treatment; D. pretreatment.
Figure 15:
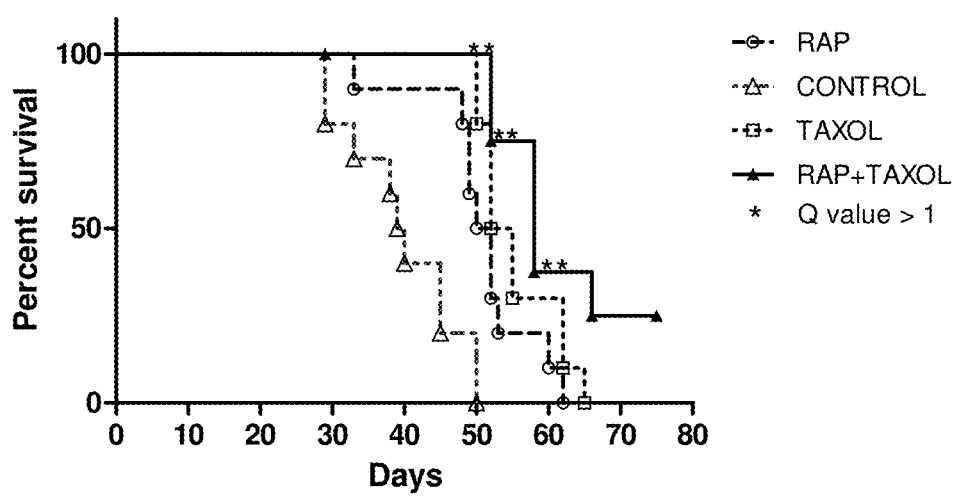
FIG. 15 shows the therapeutic effect of different combinations of compounds on survival rate of a BALB/c mice model with mammary cancer orthotopically injected with 4T1 mouse mammary cancer cells over a time course: RAP: the pharmaceutical composition of the present invention; Taxol: paclitaxel or TAXOL®; RAP+Taxol: the pharmaceutical composition of the present invention plus paclitaxel.

As illustrated by FIGS. 14a and 14b, daily feeding with either Example 1 or 5 significantly suppressed tumor growth in orthotopic 4T1 murine mammary carcinoma xenograft, without toxicity. Pretreatment with either Example 1 or 5 (group D) showed much better anticancer effect.

Example 14

Synergistic anticancer effect of combined use of the polysaccharide composition of the present invention ("RAP") and Taxol, a known chemotherapeutic agent, against the tumor growth in mice orthotopically injected with 4T1 murine mammary cancer cells. Six- to eight-week-old female BALB/c mice were divided into four groups (8-10 mice/each group): Control group and all the other three groups implanted with tumor cells (2×10$^6$) at day 7; RAP group and RAP+Taxol group daily gavaged with RAP (40 mg/kg/day) since day 0; and Taxol group and RAP+Taxol group treated with i.p. injection of Taxol (20 mg/kg/week) since day 17.

In this example, the average body weight of mice is 20 g; and the doses of Taxol and RAP are 20 mg/kg, and 40 mg/kg, respectively.

According to the commonly used Meeh-Rubner conversion formula, the dose ratio between mice and human is approximately 12:1, so the human doses of RAP and Taxol will be 3.3 mg/kg/day, and 1.6 mg/kg/week, respectively.

In details:
Human dose (mg/kg)=mice dose (mg/m$^2$)×human BSA (m$^2$)/human body weight (kg)
Human BSA=0.0061×body height (cm)+0.0128×body weight (kg)−0.1529;
Mice dose (mg/m$^2$)=mice dose (mg/kg)/mice BSA (m$^2$);
Mice BSA=9.1×(W$^{2/3}$/10000).
W represents body weight (g), BSA represents body surface area.
Suppose the average human body weight is 60 kg, the height is 170 cm, so:
Human BSA=0.0061×170+0.0128×60-0.1529=1.6521 m$^2$
Mice BSA=9.1×20$^{2/3}$/10000=0.0067 m$^2$
Mice dose (mg/m$^2$) of Taxol=20×20×10$^{-3}$/0.0067=59.7 mg/m$^2$
Mice dose (mg/m$^2$) of the RAP=40×20×10$^{-3}$/0.0067=119.4 mg/m$^2$
Therefore,
Human dose (mg/kg) of Taxol will be 59.7×1.65/60=1.64 mg/kg/week
Human dose (mg/kg) of the RAP will be 119.4×1.65/60=3.28 mg/kg/day The results indicate that the RAP, Taxol, and RAP+Taxol exhibit significant anticancer effect, compared to control group. When all the mice of Control group died at day 50, no death occurred in both Taxol and RAP+Taxol groups. More interestingly, the survival rate of RAP+Taxol group remained at 75%, while that of Taxol group dived to only 30% at Day 55. Finally, 25% of RAP+Taxol group was still alive at Day 75, which is the end of the experiment, but all mice in other groups died early before/at day 65. The Q value calculated using data of Taxol, and RAP+Taxol groups is above 1 since day 50. It is suggested that the combined use of RAP and Taxol generates synergistic anticancer effect.

INDUSTRIAL APPLICABILITY

The present invention discloses a pharmaceutical composition for modulating immune system comprising at least one polysaccharide extracted from *Radix Astragali, Radix Codonopsis, Ganoderma sinense*, or mixtures thereof, and their extraction process. It further discloses a method of modulating immune system by applying said pharmaceutical composition, and a method of preventing and/or pretreating and/or treating cancers which comprises applying said pharmaceutical composition before/during chemotherapy.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

What is claimed is:

1. A method of treating mammary cancer consisting essentially of administering a therapeutically effective amount of a mixture of *Radix Astragali* extract, *Radix Codonopsis* extract, and *Gandoderma sinense* to a human or animal.

2. The method of claim 1, wherein the mixture has a molecular weight in the range of 500-2,500 kDa.

3. The method of claim 1, wherein any two of the extracts in the mixture are in a molar ratio ranging from 1:30 to 30:1, 1:20 to 20:1, or 1:10 to 10:1.

4. The method of claim 1, wherein the *Gandoderma sinense* extract consists of glucose, galactose and mannose as constituents in a molar ratio of 4.7:27.1:1.0.

5. The method of claim 1, wherein the *Radix Astragali* extract consists of rhamnose, arabinose, glucose, galactose and galacturonic acid as constituents in a molar ratio of 0.03:1.00:0.27:0.36:0.30.

6. The method of claim 1, wherein the *Gandoderma sinense* extract consists mainly of glucose and trace amounts of galactose and mannose as constituents.

7. The method of claim 1, wherein the *Radix Astragali* extract has a hyperbranched structure.

8. The method of claim 1, wherein the *Radix Astragali* extract consists of at least one sugar residue selecting from the group consisting of 1,2,4-linked Rhap, α-1,4-linked Glcp, α-1,4-linked GalAp6Me, β-1,3,6-linked Galp, α-T-Araf, α-1,5-linked Araf, T-linked Araf, T-linked Glcp, T-linked Galp, (1→6)-linked-β-D-glucopyranosyl, (1→4)-linked-β-D-glucopyranosyl, (1→3)-linked-β-D-glucopyranosyl, non-reducing end β-D-glucopyranosyl, t-, 1,3-, 1,4-, 1,6-, 1,3,4- and 1,3,6-linked Glcp, t-linked Galp, 1,6-linked Manp, and combinations thereof.

9. The method of claim 1, wherein the *Radix Astragali* extract consists of a backbone of 1,6-linked-β-D-glucopyranosyl residues and branches at the O-3 position of every two sugar residues along the backbone.

10. The method of claim 1, wherein the *Radix Astragali* extract consists of side chains containing 1,3-, 1,4-linked-β-D-glucopyranosyl, and non-reducing end β-D-glucopyranosyl residues.

11. The method of claim 1, wherein the *Radix Astragali* extract has a protein content of 1-20% or 5-15%.

12. The method of claim 1, wherein the therapeutically effective amount of the mixture is 0.1-20 mg/kg of body weight of said human or said animal per day.

13. The method of claim 1, wherein the mixture is administered for at least 7 days before administering at least one chemotherapeutic agent to said human or said animal.

14. The method of claim 13, wherein said at least one chemotherapeutic agent is administered about 1.6 mg/kg/week when being administered in combination with the mixture in about 3.3 mg/kg/day to said human or said animal for six consecutive days prior to the administration of said at least one chemotherapeutic agent.

15. The method of claim 13, wherein said at least one chemotherapeutic agent is paclitaxel.

16. The method of claim 13, wherein the mixture is administered orally while said at least one chemotherapeutic agent is administered via intraperitoneal injection to said human or said animal.

* * * * *